United States Patent
de Vaan et al.

(10) Patent No.: US 11,915,426 B2
(45) Date of Patent: *Feb. 27, 2024

(54) METHOD, DEVICE AND SYSTEM FOR DYNAMIC ANALYSIS FROM SEQUENCES OF VOLUMETRIC IMAGES

(71) Applicant: 3mensio Medical Imaging B.V., Bilthoven (NL)

(72) Inventors: Jan Anne Niels de Vaan, Houten (NL); Peter Heil, Utrecht (NL); Arjen Witteveen, Utrecht (NL); Martijn L. Laurentius Chatrou, Son en Breugel (NL)

(73) Assignee: 3mensio Medical Imaging B.V., Bilthoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/584,023

(22) Filed: Jan. 25, 2022

(65) Prior Publication Data

US 2022/0148174 A1 May 12, 2022

Related U.S. Application Data

(63) Continuation of application No. 16/561,865, filed on Sep. 5, 2019, now Pat. No. 11,232,569.

(30) Foreign Application Priority Data

Sep. 7, 2018 (EP) .................................. 18193175

(51) Int. Cl.
*G06T 7/00* (2017.01)
*A61F 2/24* (2006.01)
(Continued)

(52) U.S. Cl.
CPC .......... *G06T 7/0016* (2013.01); *A61F 2/2418* (2013.01); *G06T 7/0012* (2013.01);
(Continued)

(58) Field of Classification Search
CPC ....... G06T 7/0016; G06T 7/0012; G06T 7/12; G06T 7/13; G06T 7/337; G06T 7/38;
(Continued)

(56) References Cited

U.S. PATENT DOCUMENTS 9,008,386 B2    4/2015 Verstraeten
11,232,569 B2 *  1/2022 de Vaan .................. G06T 15/08
(Continued)

OTHER PUBLICATIONS

"Automatic Coronary Artery Calcium Scoring in Cardiac CT Angiography Using Paired Convolutional Neural Networks", Wolternik et al, Medical Image Analysis 2016, p. 123-136.
(Continued)

*Primary Examiner* — John B Strege
(74) *Attorney, Agent, or Firm* — Gordon & Jacobson, P.C.

(57) ABSTRACT

Devices, systems, computer program products and computer implemented methods are provided for dynamically assessing a moving object from a sequence of consecutive volumetric image frames of such object, which images are timely separated by a certain time interval, by:
identifying in at least one image of the sequence the object of interest;
segmenting the object to identify object contour;
propagating the object contour as identified to other images of the sequence; and
performing dynamic analysis of the object based on the object contour as propagated.

22 Claims, 19 Drawing Sheets

(51) Int. Cl.
| | |
|---|---|
| G06T 7/12 | (2017.01) |
| G06T 7/13 | (2017.01) |
| G06T 7/33 | (2017.01) |
| G06T 7/38 | (2017.01) |
| G06T 7/62 | (2017.01) |
| G06T 7/73 | (2017.01) |
| G06T 15/08 | (2011.01) |
| G06V 10/75 | (2022.01) |

(52) U.S. Cl.
CPC .......... *G06T 7/12* (2017.01); *G06T 7/13* (2017.01); *G06T 7/337* (2017.01); *G06T 7/38* (2017.01); *G06T 7/62* (2017.01); *G06T 7/73* (2017.01); *G06T 15/08* (2013.01); *G06V 10/754* (2022.01); *G06T 2207/10016* (2013.01); *G06T 2207/10076* (2013.01); *G06T 2207/10081* (2013.01); *G06T 2207/20076* (2013.01); *G06T 2207/20101* (2013.01); *G06T 2207/30048* (2013.01)

(58) Field of Classification Search
CPC .. G06T 7/62; G06T 7/73; G06T 7/246; G06T 15/08; G06T 2207/10016; G06T 2207/10076; G06T 2207/10081; G06T 2207/20076; G06T 2207/20101; G06T 2207/30048; G06T 2207/10104; G06T 2207/10108; G06T 2207/20081; A61F 2/2418; G06V 10/754
See application file for complete search history.

(56) References Cited

U.S. PATENT DOCUMENTS

| | | |
|---|---|---|
| 2012/0076382 A1 | 3/2012 | Guetter et al. |
| 2020/0082531 A1 | 3/2020 | de Vaan et al. |

OTHER PUBLICATIONS

"Deep Learning", Lecun et al., Nature 521 (7553) (2015), p. 436-444.
"Long-term Follow-up of Percutaneous Repair of Paravalvular Prosthetic Regurgitation", Sorajji et al, J Am Coll Cardiol 2011;58:2218-24.
"Mitral Annular Dynamics in Myxomatous Valve Disease: New Insights with Real-Time 3-Dimensional Echocardiography", Grewal et al, Circulation 2010;121:1423-31.
"Multimodality Imaging in the Context of Transcatheter Mitral Valve Replacement Establishing Consensus Among Modalities and Disciplines", Blanke et al, JACC: Cardiovascular Imaging vol. 8, No. 10, 2015.
"Normal mitral annulus dynamics and its relationships with left ventricular and left atrial function", Mihaila et al, Int J Cardiovasc Imaging (2015) 31:279-290.
"Quantitative Multi-slice Computed Tomography Assessment of the Mitral Valvular Complex for Transcatheter Mitral Valve Interventions Part 1: Systematic Measurement Methodology and Interobserver variability", P. Theriault-Lauzier et al, EuroIntervention. Oct. 10, 2016;12(8): e1011-e1020.
"Quantitative Multi-slice Computed Tomography Assessment of the Mitral Valvular Complex for Transcatheter Mitral Valve Interventions Part 2: Geometrical Measurements in Patients with Functional Mitral Regurgitation", P. Theriault-Lauzier et al., EuroIntervention. Oct. 10, 2016;12(8): e1021-e1030.
'Semi-Automatic Tracking for Mitral Annulus Dynamic Analysis Using Real-Time 3D Echocardiography; Veronesi F. et al., Computers in Cardiology 2006;33-113-116.
"A Survey of Medical Image Registration" Maintz et al., Medical Image Analysis (1998) vol. 2, No. 1, pp. 1-36.
"The Surveyor's Area Formula, Braden," The College Mathematics Journal 1986. 17 (4): 326-337.
"Three-Dimensional Echocradiographic Anaylsis of Mitral Annular Dynamics", Levack et al., Circulation, 2012; 126: S183-S188.
European Search Report dated Feb. 8, 2019 of Application No. EP18193175.

* cited by examiner

METHOD, DEVICE AND SYSTEM FOR DYNAMIC ANALYSIS FROM SEQUENCES OF VOLUMETRIC IMAGES

CROSS-REFERENCE TO RELATED APPLICATION(S)

The present disclosure is a continuation of U.S. application Ser. No. 16/561,865, filed on Sep. 5, 2019, which claims priority from EP18193175, filed on Sep. 7, 2018, entitled "METHOD, DEVICE AND SYSTEM FOR DYNAMIC ANALYSIS FROM SEQUENCES OF VOLUMETRIC IMAGES," both of which are herein incorporated by reference in their entireties.

BACKGROUND

1. Field

The present disclosure relates to the field of medical interventions, and, in particular, to the field of heart valve replacements and repairs.

2. State of the Art

When it comes to transcatheter mitral valve replacement (TMVR) and repair, computed tomography (CT) has an important role in pre-operative patient and device selection by determining the dynamic changes as well as the exact anatomy and geometric measurements of the mitral valve annulus as described by Mihaila et al, "Normal mitral annulus dynamics and its relationships with left ventricular and left atrial function", Int J Cardiovasc Imaging (2015) 31:279-290.

Currently, several mitral valve replacement devices are in various stages of development and a wide range of repair and replacement treatment options are available to overcome problems such as regurgitation caused by a diseased valve.

A pre-operative analysis of the mitral valve (consisting of the annulus, leaflets and the like) and surrounding structures, such as for instance the left ventricle outflow tract, based on information obtained from CT datasets is valuable for clinicians as it helps the clinician to better understand the complex structure of the mitral valve as shown in FIG. 1.

In addition to the complex structure of the mitral valve, the valve is also subject to geometric deformation during the cardiac cycle. For a clinician to obtain a complete overview of all aspects concerning the mitral valve without an accurate analysis has been proven to be extremely difficult.

Information obtained from a pre-operative analysis, for instance by CT, can for instance aid the clinician in choosing the most appropriate therapy for the patient (for instance valve replacement or valve repair therapy).

If for example the ratio between the diameter of major and minor axis (elliptical shape) of the valve is too large, then the clinician might prefer a valve repair therapy instead of a valve replacement therapy as most valve implants have a rounded shape.

Besides the choice of which type of therapy is best for the patient, the information obtained from a pre-operative analysis is also needed to aid in the choice of devices used during such therapy.

In the case of a valve repair therapy such as annuloplasty, where the valve leaflets are pulled together (cinching) to facilitate leaflet coaptation, the expected percentage of cinching that is needed to obtain full coaptation is determinative for ring choice as each ring has a maximum percentage of cinching that it can perform.

In the case of TMVR therapy the type and size of the valve implant must be chosen in such a manner that the implant is able to resist frame fracture and avoid perforation to be durable. Also, interaction with adjacent structures (for instance the coronary sinus) and anchoring mechanisms is requisite to prevent embolization.

Furthermore, if a relatively large valve implant is most suitable for the patient, the patient can be at risk for paravalvular regurgitation (leakage) in the case of disproportionate short-axis diameter enlargement as described by Sorajja et al, "Long-term follow-up of percutaneous repair of paravalvular prosthetic regurgitation", J Am Coll Cardiol 2011; 58:2218-24 or left ventricular outflow tract obstruction in the case of disproportionate major axis diameter enlargement.

In all the above mentioned examples accurate and complete information regarding mitral valve anatomy, geometry and dynamics are crucial for preserving normal mitral valve function.

In current practice the pre-operative analysis using CT data is performed by three dimensional (3D) segmentation of the mitral annulus. This is done using reformatted image slices in which the clinician can indicate multiple points through which a spline can be fitted as described by Blanke et al, "Multimodality Imaging in the Context of Transcatheter Mitral Valve Replacement Establishing Consensus Among Modalities and Disciplines", JACC: Cardiovascular Imaging Vol. 8, No. 10, 2015 by the American College of Cardiology Foundation. The placement of these points by the clinician is done on one phase of the cardiac cycle as can be seen in FIG. 2.

As the mitral annulus is a dynamic structure (during the cardiac cycle), it is important that multiple heart phases enclosing the cardiac cycle are analyzed to obtain a complete overview for the clinician. As the 3D segmentation of the mitral valve's annulus is a time consuming process that is also prone to errors, usually a maximum of two heart phases are analyzed. The 3D mitral annulus segmentation is for instance performed at end diastolic (ED) heart phase (MV opening) and at end systolic (ES) heart phase (MV closing) within the heart cardiac cycle.

This process thus only provides static information of the valve anatomy at two specific phases within the cardiac cycle. However, in healthy subjects, large dynamic changes can be observed regarding geometry of the mitral annulus, for instance, in intercommisural diameter (FIG. 1, 102). The extent of these changes are also related to the left ventricle and left atrium function as described by Mihaila et al, "Normal mitral annulus dynamics and its relationships with left ventricular and left atrial function", Int J Cardiovasc Imaging (2015) 31:279-290. For instance in patients with functional mitral regurgitation, dynamic mitral annular geometry differences are minimal, whereas these differences are more pronounced in patients with degenerative mitral valve disease (DMVD) as described by Grewal et al, "Mitral annular dynamics in myxomatous valve disease: new insights with real-time 3-dimensional echocardiography", Circulation 2010; 121:1423-31. An example of this can be seen in FIG. 3.

When performing static analysis as mentioned above in the ED and the ES phase, important information can be overlooked. For instance for the anterior-posterior diameter as shown in FIG. 3, the maximum diameter is not obvious in the ED and ES phase for patients with DMVD. This missing maximum diameter is essential for the correct choice of therapy and device.

These potential changes in mitral annular dimensions emphasizes the importance of multiphasic dynamic annular measurements pre-operative planning as described by Blanke et al, "Multimodality Imaging in the Context of Transcatheter Mitral Valve Replacement Establishing Consensus Among Modalities and Disciplines", JACC: Cardiovascular Imaging, Vol. 8, No. 10, 2015: 1191-1208.

Thus, there is a need for a quick and accurate method that automatically provides both geometric and dynamic analysis of the heart valve's annulus containing multiple heart phases within the cardiac cycle.

SUMMARY

It is thus an object of embodiments herein to provide improved devices, systems, computer program products and computer implemented methods that are configured to obtain the needed dynamic information over multiple phases of the heart cycle quickly and accurately by performing multiphase analysis of one or multiple valves to be able to determine the dynamic changes and the measurements needed for good decision making in the field of valve replacement and/or repair.

In accordance with embodiments herein, devices, systems, computer program products and computer implemented methods are provided for dynamically assessing a moving object from a sequence of consecutive volumetric image frames of such object, which images are separated in time by a certain time interval. The images can be part of a four-dimensional (4D) CT dataset, which includes 3D CT data acquired over time. The devices, systems, program products and methods can involve one or more computer systems configured with specific executable instructions that perform the following:
  a) identifying in at least one image of the sequence the object of interest;
  b) segmenting the object to identify object contour;
  c) propagating the object contour as identified to other images of the sequence;
  d) performing dynamic analysis of the object based on the object contour as propagated.

The object of interest is typically a heart valve with the images referring to different phases of the heart cycle.

The operation of segmenting the object may advantageously include:
  receiving from a user a seed point indicating the center of the object of interest;
  using the seed point to determine an axis of the object (for example, the long axis of a valve);
  determining a cost image representing the probability a voxel belongs to the object contour (for example, the valve annulus);
  finding minimal cost path to identify the contour within the cost image; and
  transforming the points of the minimal cost path to 3D patient coordinates to obtain the 3D contour of the object of interest.

According to an embodiment, the valve is a mitral or a tricuspid valve, the long axis of the valve being determined by using the seed point to estimate the location of the apex point of the left or right ventricle and the center-lumen line within the ventricle optionally adjusting the center-lumen line towards the center of mass of the ventricle blood pool.

The cost image may have advantageously the form of a matrix wherein columns represent a distance along the long-axis line in which the center column corresponds to the position of the seed point on the long-axis line and rows represent the degree of rotation around the long-axis line, wherein the value of each element of the cost image corresponds to the distance from the long-axis line to the edge of the blood lumen for a combination of distance along the long-axis line and an angle.

According to an embodiment, the points on the valve annulus are corrected using annulus seeding points and calculating for each seeding point a cross-sectional plane containing the valve center, for example, allowing the cross-sectional plane to move along the normal vector of such cross-sectional plane.

Advantageously, any adjustment of the points on the valve annulus within the cross-section view or the cross-sectional plan view or volume rendered view is automatically transferred to all views.

According to an embodiment, propagating the object contour comprises registering all or part of the images of the sequence to find a transformation, for example a non-rigid transformation to best model the changing shape of the heart, and apply such transformation to contour points of the segmented object to find corresponding locations in other images of the sequence.

The registration may be advantageously performed on a sub volume within the sequence of images, such sub volume being user defined or automatically extracted based on the location of the object of interest as segmented.

According to embodiments here, the dynamic analysis comprises calculating one or more parameters related to geometry and/or geometry deformation of the object of interest in a plurality of images of the sequence.

By way of example, such parameters are selected from the group consisting in: anteroposterior (AP) diameter, intercommissural (CC) diameter, annulus height, perimeter of the annulus, projected area of the annulus, projected perimeter of the annulus.

According to an aspect there is also a computer product directly loadable into the memory of a digital computer and comprising software code portions for performing the method according to embodiments herein when the product is run on a computer.

Embodiments also provide for an X-ray apparatus, for example a CT apparatus, for acquiring a series of three-dimension images, the apparatus comprising means for obtaining a cine of consecutive image voxels of the heart of a patient, the apparatus further comprising processing means programmed for performing the method according to embodiments herein to perform a dynamic analysis of a valve of the heart.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION OF ILLUSTRATIVE EMBODIMENT(S)

Figure 4:
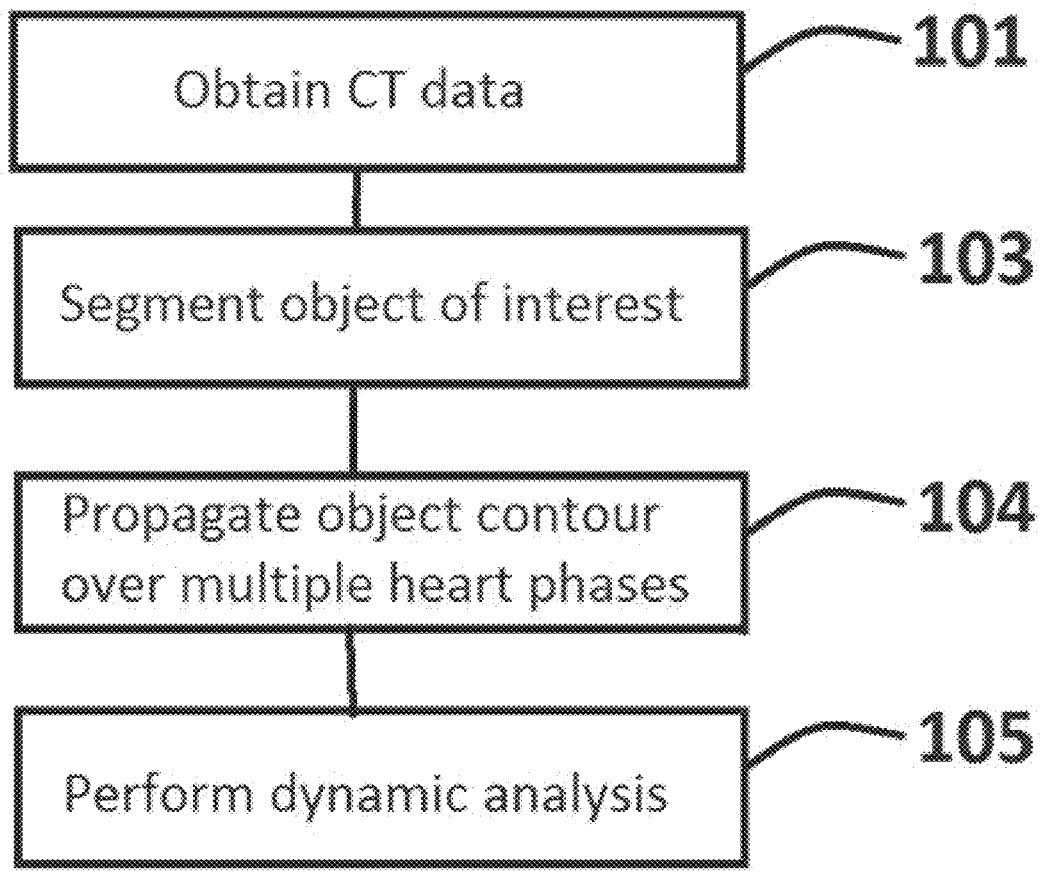
FIG. 4 shows an exemplary flow chart of an embodiment of the present application.

FIG. 4 shows a flow chart illustrating the operations according to an embodiment of the present application. The operations employ an imaging system capable of acquiring and processing CT images of an organ (or portion thereof) or other object of interest.

Figure 5:
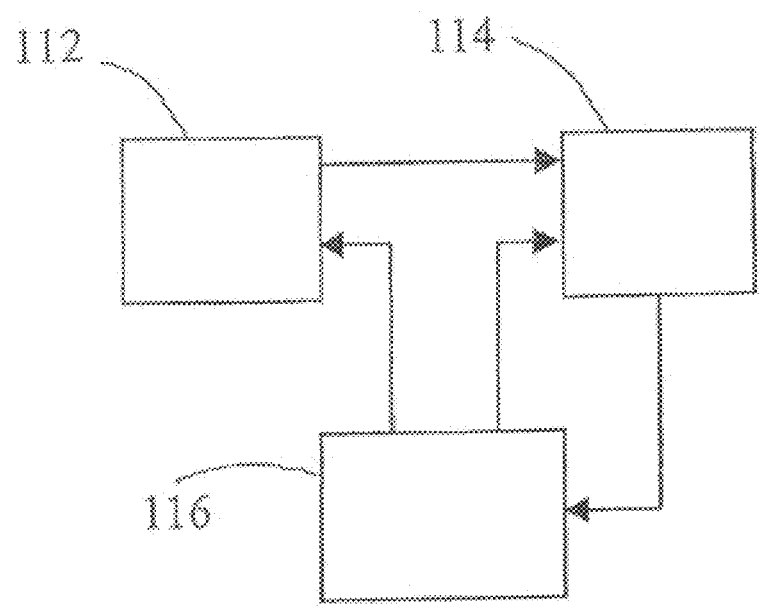
FIG. 5 shows a functional block diagram of an exemplary X-ray CT system.

FIG. 5 is a functional block diagram of an exemplary X-ray CT system, which includes a CT imaging apparatus 112 that operates under commands from user interface module 116 and will provide data to data processing module 114. The X-ray CT imaging apparatus 112 captures a CT scan of the organ of interest over multiple heart phases (3D+time). The X-ray CT imaging apparatus 112 typically includes an X-ray source and detector mounted in a rotatable gantry. The gantry provides for rotating the X-ray source and detector at a continuous speed during the scan around the patient who is supported on a table between the X-ray source and detector.

The data processing module 114 may be realized by a personal computer, workstation or other computer processing system. The data processing module 114 processes the CT scan captured by the X-ray CT imaging apparatus 112 to generate data as described herein.

The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of FIG. 4 as described below.

The operations of FIG. 4 can also be carried out by software code that is embodied in a computer product (for example, an optical disc or other form of persistent memory such as a USB drive or a network server). The software code can be directly loadable into the memory of a data processing system for carrying out the operations of FIG. 4.

In this example it is assumed that the imaging system has acquired and stored at least one 4D (3D+time) CT dataset of an object of interest. Any imaging device capable of providing an X-ray CT scan can be used for this purpose.

The present application is particularly advantageous in heart valve analysis based on a 4D CT dataset and it will mainly be disclosed with reference to this field, particularly for valve replacement and repair.

An embodiment of the present application is now disclosed with reference to FIG. 4. The therein-depicted steps can, obviously, be performed in any logical sequence and can be omitted in parts. For exemplary purposes this embodiment is disclosed with reference to the mitral and tricuspid valve, however the embodiment is applicable for any one of the four heart valves (aortic, mitral, tricuspid and pulmonary).

As described in step 101 of FIG. 4, a contrast enhanced 4D (3D+time) CT dataset is obtained. The 4D CT dataset can be obtained from a database or acquired directly from a CT imaging modality. The 4D CT dataset consists of multiple 3D volumetric datasets of the object of interest, each for a certain heart phase. Each volumetric dataset consists of multiple image slices each belonging to the same heart phase.

Within step 103 of FIG. 4, the object of interest needs to be segmented in one of the heart phases within the obtained 4D CT dataset. This can be done manually or (semi) automatically.

Manual segmentation of the object of interest involves manual identification of the 3D valve annulus, which is the saddle-shaped mitral annulus in case of the mitral valve. Since the valve's annulus are complex 3D structures, manual identification of the valve annulus is not straight forward. A way to support the clinician in manual identification of the valve annulus is by allowing a stepwise rotation along a long-axis reformatted image within the CT dataset. In case of identifying the mitral valve, the long-axis is defined by a line through the left ventricular apex position (FIG. 7, 702) and a point representing roughly the center of the mitral valve (FIG. 7, 701). Such long-axis can be defined by manual identification of left ventricular apex position and center of the mitral valve, or by (semi) automatic approaches for instance as described by step 601, 602 and 603 of FIG. 6. The long-axis reformatted image is created by reformatting along a plane which intersect the long-axis line. The stepwise rotation is performed by rotating this plane 360/n degrees around the long-axis line after the clinician identified in the long-axis reformatted image a seed point representing the valve annulus position. With this approach the 3D shape of the valve annulus is defined by a number of seeding points in which a 3D curve is fitted. Typically the number of seed points is between ten and sixteen seeding point (n). After placing the seeding points and thus tracing the annulus, the annulus can be edited according to the annulus anatomy, if needed. Editing of the annulus can for instance be performed by adjusting the height (z coordinate of the 3D position) of the seeding point within the long-axis view and adjustment of the x,y coordinate of the 3D position in a view perpendicular to the long-axis view, for instance by the method as presented by FIG. 19.

Figure 6:
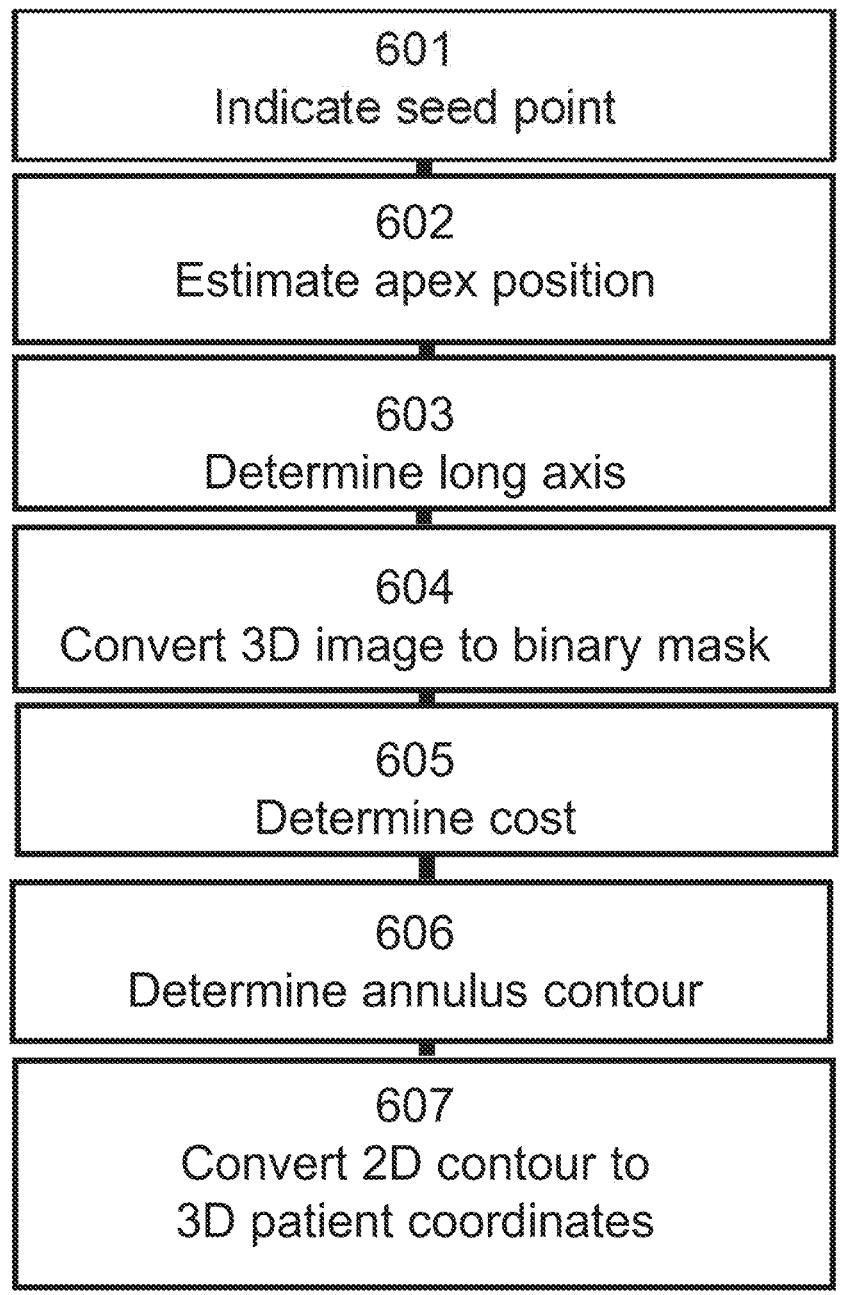
FIG. 6 shows an exemplary flow chart for semi-automatic annulus segmentation.
Figure 7:
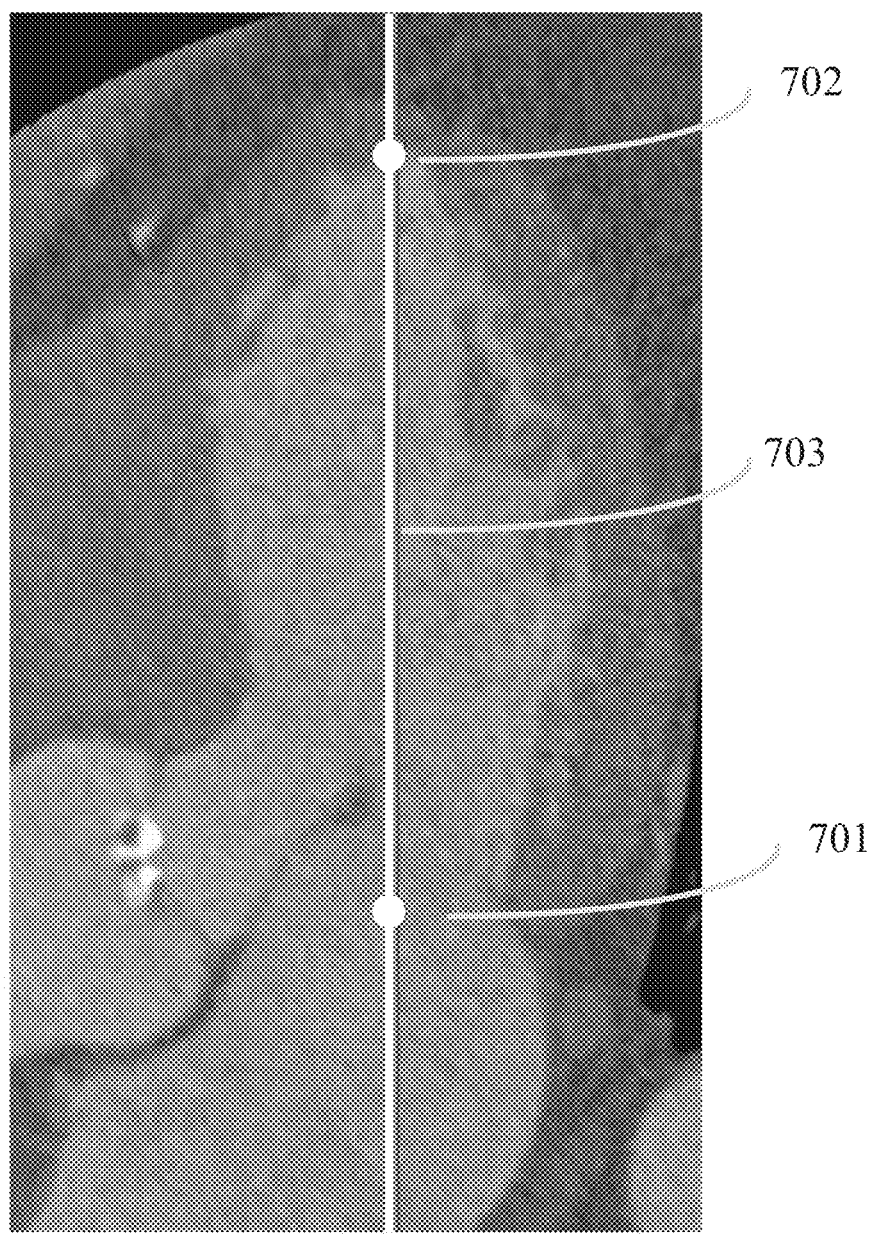
FIG. 7 shows the user indicated position of the mitral valve as well as the determined long axis line.

For the (semi) automatic method reference is made to FIG. 6. Within step 601 of FIG. 6, the clinician first provides a seed point that indicates the center of the valve of interest (FIG. 7, 701). For explanation the mitral valve is used. This seed point, the result of step 601, is then used to estimate the location of the apex point of the ventricle as described in step 602 of FIG. 6. This is done to determine the long-axis line. For mitral valve this long-axis line represents the left side of the heart (left atrium & ventricle). To determine the apex point location, first an estimated center-lumen line within the ventricle is defined. Using heuristics, the direction where the apex point is located is determined. The center-lumen line runs from the user indicated seed point towards the apex within the ventricle. Using ray-casting, the ventricular blood pool boundary is calculated on planes orthogonal to the center-lumen line. The center-lumen line is adjusted towards the center of mass of the ventricle blood pool. Ray-casting and adjusting the center-lumen line is repeated until the center-lumen line is stable, or until a maximum number of iterations is reached.

Within step 603 the long-axis line (FIG. 7, 703) of the left side of the heart is then determined as a line through the seed point (FIG. 7, 701) and the optimized apex position (FIG. 7, 702). Optionally this long-axis line may be adjusted by the clinician.

Within step 604 of FIG. 6, a binary mask is determined to identify which voxels belong to the blood lumen or not. Using the voxel values on and close to the seed point (FIG. 7, 701) and the long-axis line (FIG. 7, 703), it can be determined which voxels belong to the blood lumen. This is done to establish a mapping function from voxel value to estimated part of blood lumen. Using this mapping function, the 3D image is converted to a 3D binary mask (where 1 means part of lumen, 0 means not). The 3D binary mask may contain 0 values inside the blood lumen that correspond to scan noise, or parts of the mitral leaflets. These noise results and artifacts can be suppressed using image processing techniques such as morphological closing. In the description of step 604, the mapping function is a 3D binary mask, but other mapping methods may be used to represent the likelihood of each voxel value within the 3D image being part of blood lumen.

Figure 8:
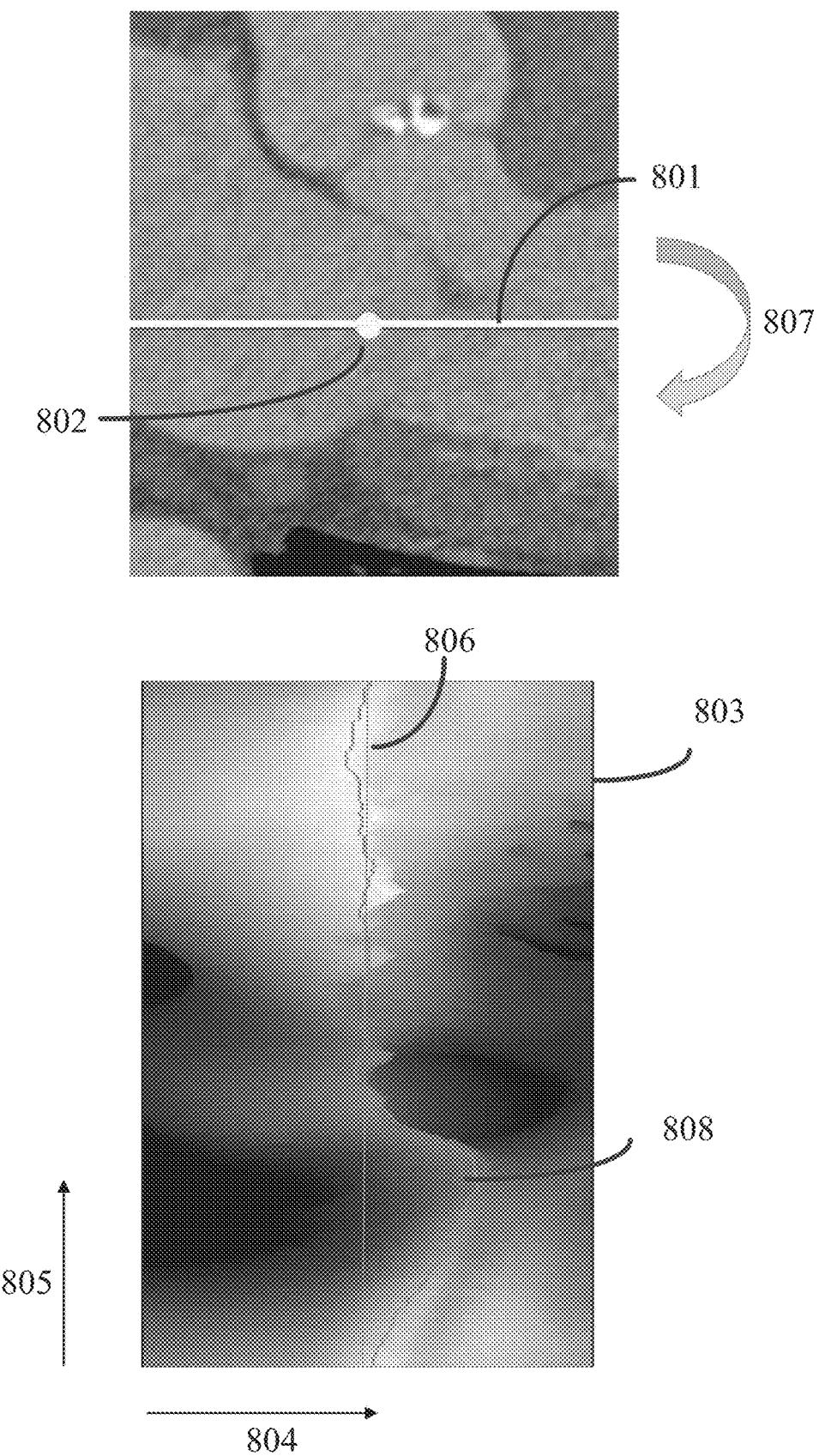
FIG. 8 shows an example of the determined cost field, including the optimal line through the cost image.

Within step 605 of FIG. 6, a cost is determined which represents the probability of a voxel represents the valve annulus. For this a cost image (FIG. 8, 803) is created as presented in FIG. 8. The columns (FIG. 8, 804) of this cost image represents a distance along the long-axis line (FIG. 8, 801, FIG. 7, 703), in which the center column (FIG. 8, 806) corresponds to the position of the seed point (FIG. 8, 802, FIG. 7, 701) on the long-axis line. The total number of columns can be predefined or may depend on the valve of interest as well as the spatial resolution of the CT dataset. The rows (FIG. 8, 805) of the cost image (FIG. 8, 803) represents the degree of rotation (FIG. 8, 807) around the long-axis line (FIG. 8, 801). Typically, the number of rows is 360 representing a stepwise rotation of one degree around the long-axis line. In general if M is the rotation step size, the number of rows will be 360 divided by M. The value of each element within the cost image corresponds to the distance from the long-axis line to the edge of the 3D binary mask, for a combination of distance along the long-axis line (FIG. 8, 804), and an angle (FIG. 8, 805). This value can be computed by ray-casting from each point, orthogonal to the long axis line, and calculating the length of the ray until it strikes the edge of the binary mask. The ray-casting may be enhanced by using the source volume pixels in addition to the binary mask. The cost image may be post processed, for instance by mapping the pixel value (that denotes a distance) to a nonlinear cost value.

Within step 606 of FIG. 6, the annulus contour is defined within the cost image. Since the annulus is an elliptical/circular structure, a close path needs to be defined within the cost image. With a closed path, any path is meant that starts 0 degrees and runs to 360 degrees at the same distance along the long-axis line. This means that within the cost image (803), a path needs to be extracted in which the column position at the first row should be equal to the column position of the last row. Finding the minimal cost path can be done by using for instance dynamic programming. An example of the cost image, including the optimal path through the cost image (808) is shown in FIG. 8. In this figure white implies low cost, dark implies high cost.

After the annulus contour (the optimal path (808)) has been established within the cost image, all points on the optimal path, combined with the established distance, are transformed to 3D patient coordinates, representing the 3D annulus contour of the valve, as described in step 607 of FIG. 6. The resulting 3D annulus contour can be simplified to remove noise and to make it easier to correct for the clinician. For instance, a number of equidistant seeding points, for instance 16, can be extracted from the 3D annulus contour, allowing easy manual editing of the 3D annulus contour as described previously in the section manual segmentation of the object of interest.

The method as presented above can also be used as a fully automatic segmentation. The only difference is that the initial long-axis is not indicated by the clinician, but is calculated from the scan by automatic labeling of structures such as the valve and the apex by use of a machine learning algorithm.

Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs.

Machine-learning is employed in a range of computing tasks where designing and programming explicit algorithms is infeasible. Machine-learning algorithms are widely used for processing of natural images (LeCun et al, "Deep learning", Nature 521 (7553) (2015), p 436-444) and since recently also in medical image analysis for classification and segmentation tasks, as for example provided by Wolterink et al, "Automatic coronary artery calcium scoring in cardiac CT angiography using paired convolutional neural networks", Medical Image Analysis 2016, p 123-136.

Given a dataset of images (e.g. cardiac CT slices) with known class labels (e.g. location of the valve(s) and apex within these cardiac CT slices), machine-learning system can predict the class labels of new images. There are at least two parts to any such system. The first part of the machine-learning is a feature extraction (extractor), being an algorithm for creating a feature vector given an image. A feature vector comprises a series of factors (e.g. multiple numbers) that are measured or extracted from the image dataset(s), which describe or characterize the nature of the object of interest, in our case the valve(s) of the heart. These features are then used by the second part of the system, a classifier, to classify unseen feature vectors extracted from the unseen image. Given a (large) database of images and extracted feature vectors whose labels are known and were used beforehand to train the machine-learning algorithm, classifying unseen images based on the features extracted the same way as in images with (known) labels (training images) is possible.

The features characterizing the valve(s) and apex are extracted from the cardiac CT slices. For this, any engineered characteristic that describes the valve(s) texture (e.g. Gaussian, Haralick texture features) can be used. Also, valve(s) features as extracted by means of encoding methods such as convolution auto-encoder can be used. Any combination of these features can be selected. Convolutional autoencoder (CAE) is a technique for extracting features from image data. The aim of an auto-encoder is to learn a representation (encoding) for a set of data, typically for the purpose of dimensionality reduction.

An auto-encoder is based on the encoder-decoder paradigm, where an input is first transformed into a typically lower-dimensional space (encoder part) and then expanded to reproduce the initial data (decoder part). It is trained in supervised or unsupervised fashion allowing it to extract generally useful features from unlabeled data, to detect and remove input redundancies and to present essential aspects of analyzing data in robust and discriminative representations. A CAE compress all the data from an image to a small vector from which it must contain enough information to reconstruct the image by the decoder. By this, the encoder is forced to learn features about the image being compressed.

Once the object of interest has been segmented, the object contour can be propagated over multiple heart phases of one or more cardiac cycles as shown in step 104 of FIG. 4.

This propagation step can for instance be done (semi) automatically based on image registration. In such case points of the 3D annulus contour is propagated from one phase within the 4D CT dataset (the source phase) to another phase within the 4D CT dataset (the target phase), while compensating for the motion of the heart between those image slices. The output consists of a new set of 3D annulus contour points on the target phase that correspond to the same anatomical location as those of the original 3D annulus contour points on the source phase.

There are many different methods for registering medical data as described by J. A. Maintz and M. A. Viergever, "A survey of medical image registration", Medical image analysis, vol. 2, no. 1, pp. 1-36, 1998. This class of methods purpose to find the transformation between a fixed image and a moving image by maximizing a chosen similarity measure (or minimizing a dissimilarity measure). This similarity measure can for instance work on the original grey values of the images. When using image registration, a plethora of possible parameters can be considered, for instance: dimensionality (e.g., 2D, 3D, or a combination), matching method (e.g., template-based, feature-based), similarity metric (e.g., normalized cross-correlation, mutual information), transformation model (e.g., rigid, non-rigid), interpolation method (e.g., nearest neighbor, linear interpolation), sampling strategy (e.g., full image, random, multi-resolution), search method (e.g., exhaustive, gradient descent). The image registration can be performed in 3D or in 2D.

The transformation found by registration is then applied to the 3D annulus contour points of the source phase to find their corresponding locations in the target phase.

The registration can be performed on the entire volume or a sub volume within the 4D CT dataset. Such sub volume can be user defined or automatically extracted based on the location of the object of interest as a result of step 103 of FIG. 4. Preferably the registration method should work with a non-rigid transformation to best model the changing shape of the heart, but a rigid transformation is also possible.

Figure 3:
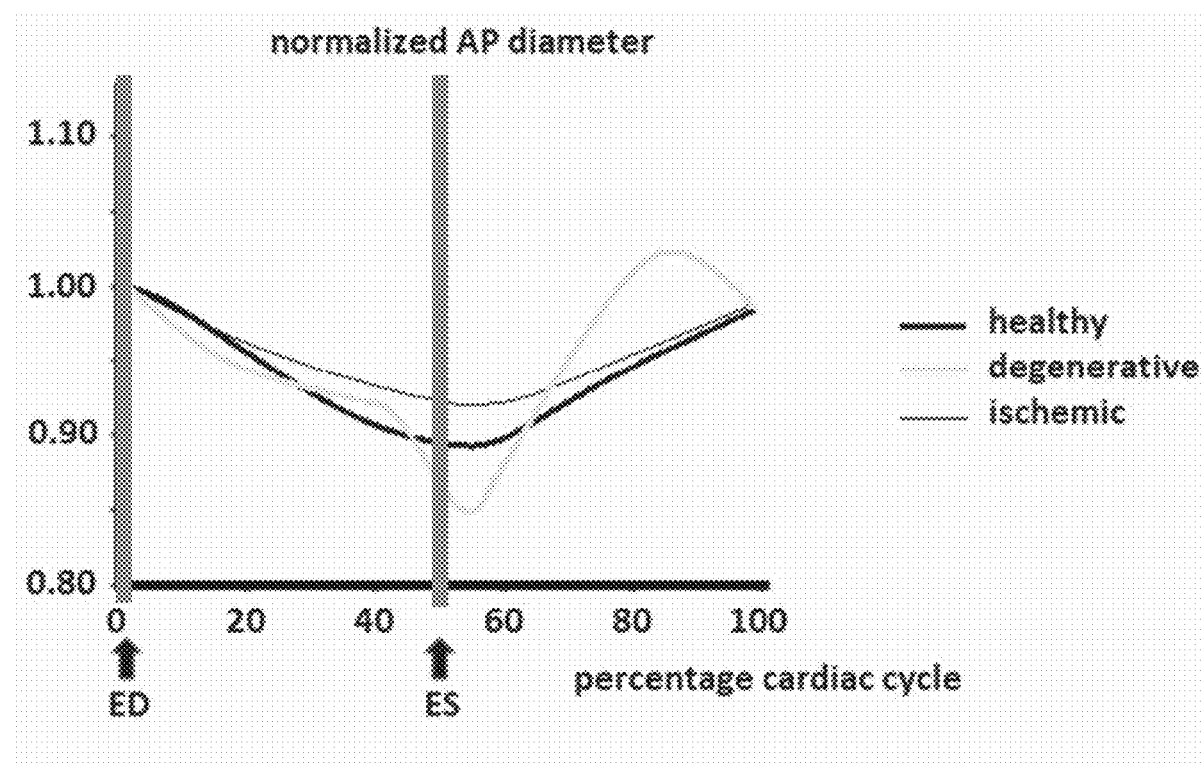
FIG. 3 shows an example of dynamic mitral annular geometry differences regarding the normalized AP diameter in healthy, ischemic and degenerative patients.

In general it is assumed that the start phase and end phase on which the propagation has to be performed are indicated by the clinician. Typically, the start phase is the phase within the 4D CT dataset in which the object of interest (FIG. 3, 103) is defined, and all remaining phases within the 4D CT dataset are propagated as described above. Optionally alternatives are also possible. For instance, direct propagation from nearest source phase. In this case an end phase is selected by the clinician and the nearest source phase is then automatically detected with known annulus landmarks.

Another alternative is propagation through intermittent phases from the nearest source phase. In this case the nearest source phase with known annulus landmarks is automatically detected. This nearest source phase is phase p within the 4D CT dataset. Propagation is then performed from phase p to p+1, from p+1 to p+2, and so on, or alternatively, p to p−1, p−1 to p−2, and so on, until the target phase is reached.

The algorithm can also identify the phases where there is less certainty (based on large differences in movement of neighboring points, discrepancies in predictions from different phases, and the absence of a clear feature match.)

Optionally the clinician has the possibility to correct the propagated annulus contour in one or multiple phases.

Figure 19:
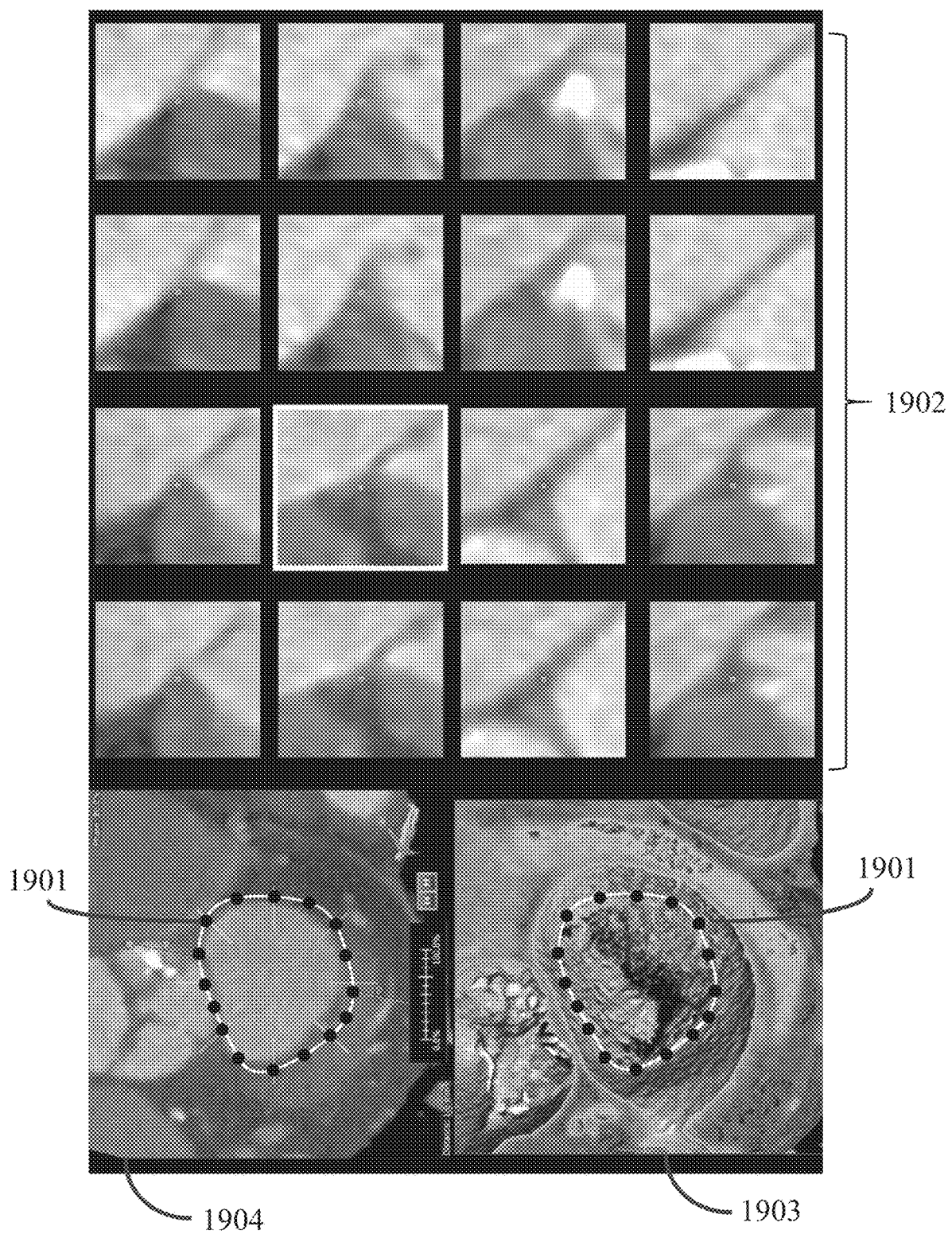
FIG. 19 shows an example of manual editing of the annulus contour in 3D/4D.

In current practice, each (control) point on the valve annulus is corrected individually. Manually editing an annulus in 3D is optimized as shown in FIG. 19. For this, a number of seeding points are defined (FIG. 19, 1901) on the 3D annulus contour, for instance by the methods described in step 607 of FIG. 6. For each seeding point on the 3D annulus, a cross-sectional plane is shown (FIG. 19, 1902). To calculate this plane, we use the annulus plane center and normal. The plane is centered around the seeding point, and tilted such that it contains the valve center, and is parallel to the valve normal.

The clinician can compare all annulus seeding points at once to make sure they make a consistent decision. Any adjustments can be performed in the cross-sectional planes (FIG. 19, 1902), the cross-sectional view (FIG. 19, 1904) or the volume render view (FIG. 19, 1903). When adjusting the annulus seeding point(s) in one of these views, the adjusted position is automatically transferred into the other views. For example, changing the x,y (in-plane) position of a seeding point within a cross-sectional planes (1902), will also change the x,y position of the applicable seeding point in view (1904) and (1903). To allow verification and correction of the z position (with respect to the cross-section plane), the z-position used for reformatting the cross sectional plane can be changed by, for instance, scrolling with the mouse wheel. Changing the z-position compromises adjusting the height of the cross-section plane, which is accomplished by allowing movement of the cross-section plane along the normal vector of the cross-sectional plane. Furthermore, by allowing 4D cine playback in the cross-sectional view(s), the clinician can check the consistency of all the annulus points during the cardiac cycle. Within FIG. 19, 1903 represents a volume render view, showing the mitral valve, and the seeding points (FIG. 19, 1901), as viewed from the atrium. All tissue in front of the valve is clipped away and blood is rendered transparent. The view shows the same location/orientation as the cross-sectional view (FIG. 19, 1904).

After propagating the 3D annulus contour over multiple image slices, dynamic analysis can be performed as described in step 105 of FIG. 4. To provide as much information as possible to the clinician, several parameters regarding annulus anatomy and geometry and geometry deformation can be taken into account.

Figure 1:
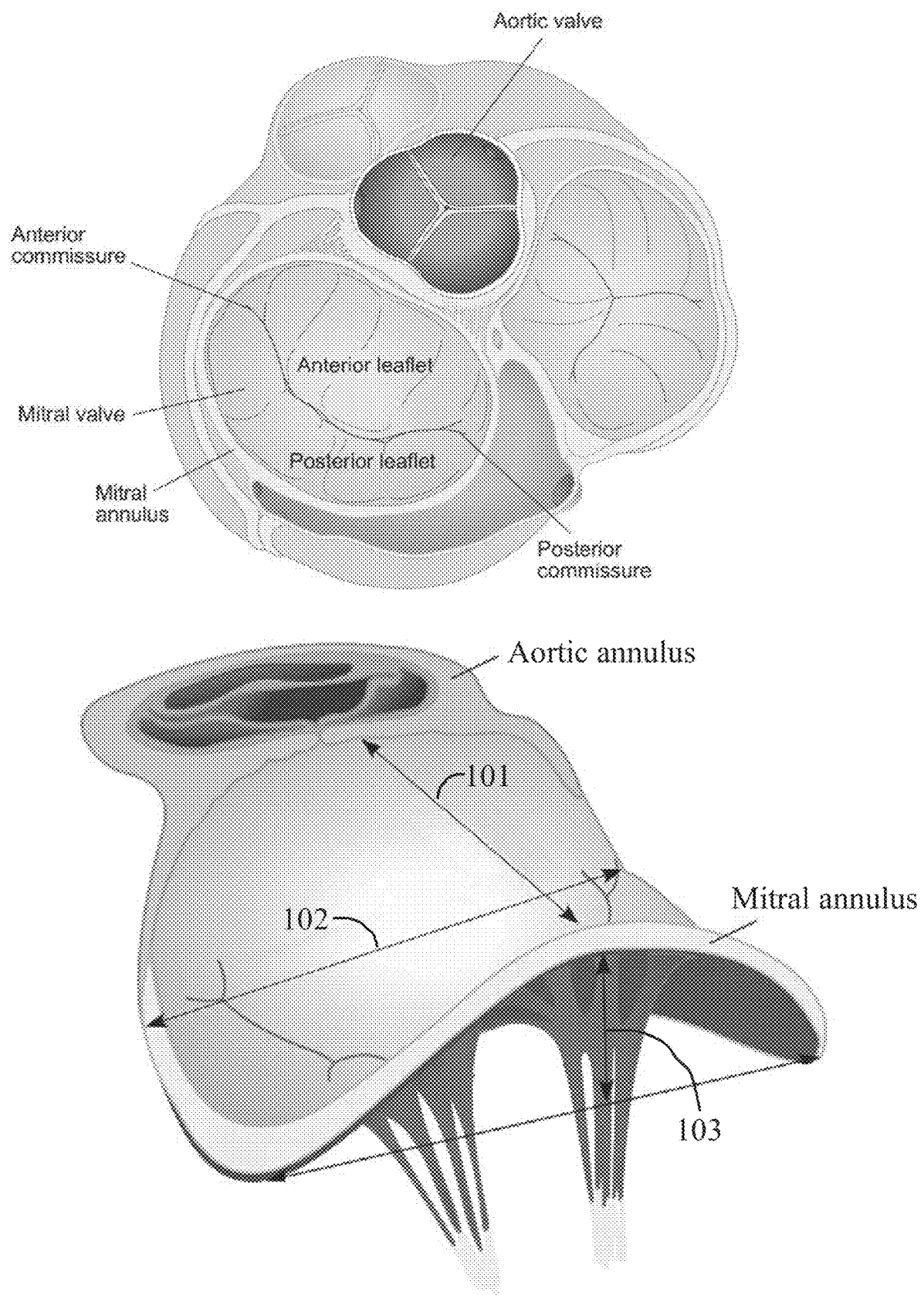
FIG. 1 shows the complex structure of the mitral valve including some important geometric parameters.
Figure 2:
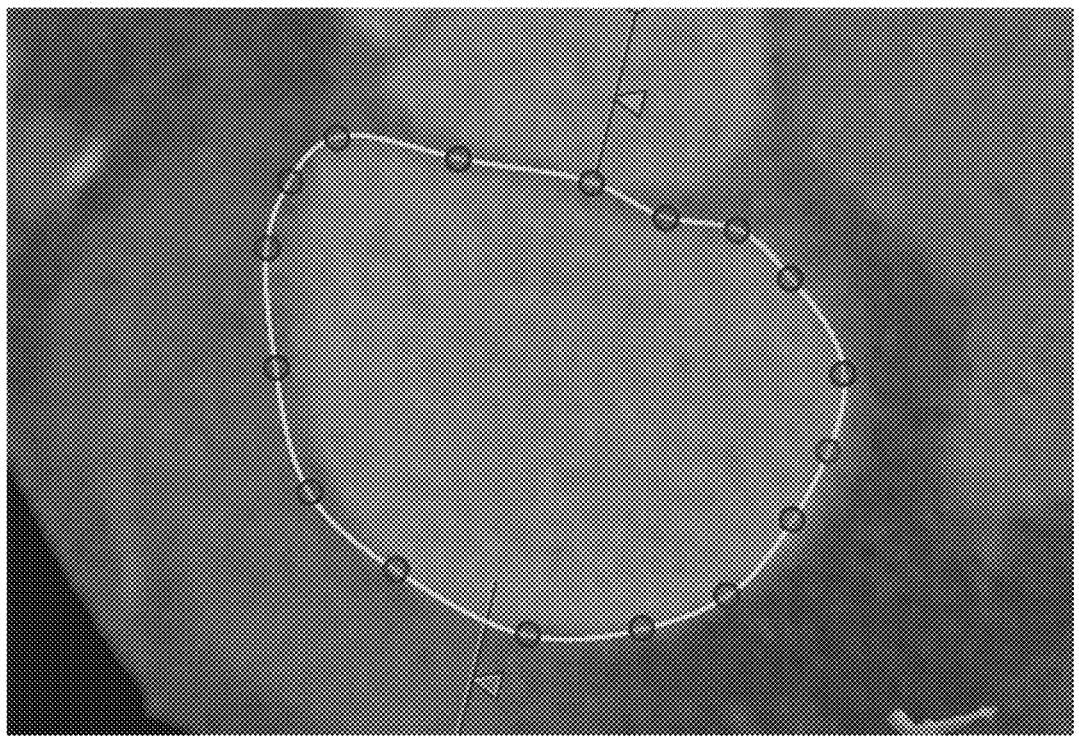
FIG. 2 shows the clinical practice concerning manual mitral annulus segmentation.

For instance, the anteroposterior (AP) diameter can be extracted from the 3D annulus contour within each phase based on the result of step 104 of FIG. 4. The AP diameter is defined as the distance between the most anterior and the most posterior point of the mitral annulus through the center of the mitral annulus as can be seen in FIG. 1, 101. In a CT dataset, the patient and image information is stored in a Digital Imaging and Communications in Medicine (DICOM) standard. The anterior and posterior patient position can be extracted from the DICOM information of the CT data.

During the cardiac cycle in healthy subjects the AP diameter has a saddle shaped response and is at its minimum when the mitral valve closes (end systole). However, for patients suffering from ischemia or myxomatous the AP diameter response during the cardiac cycle can differ. In ischemic patients the AP diameter response is flatter due to less motion and contraction. In contrast, myxomatous annuli appear to demonstrate rapid systolic dilatation compared with normal and ischemic annuli as described by Levack et al "Three-Dimensional Echocradiographic Analysis of Mitral Annular Dynamics", Circulation, 2012; 126: S183-S188.

Figure 9:
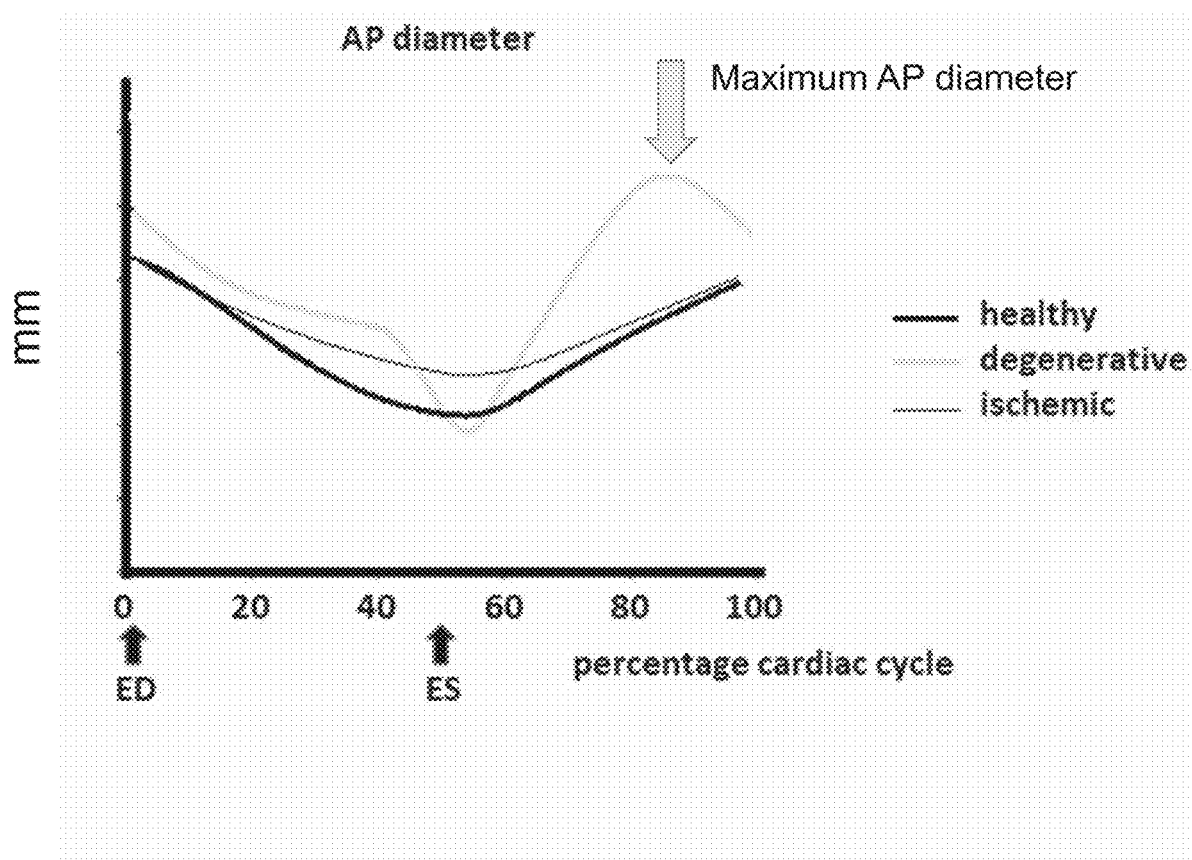
FIG. 9 shows the determined dynamically changing AP diameter and the corresponding maximum AP diameter in the case of a myxomatous patient.

Additionally, in diseased patients the AP diameter is often larger than in healthy patients which makes the AP diameter also an important parameter for device sizing. The maximum AP diameter for myxomatous patients as shown in FIG. 9 is used by the clinician for instance as a measure for the size of the valve implant.

Another important parameter is the intercommissural (CC) diameter. Two perpendicular diameters of the mitral valve are measured: the anteroposterior (FIG. 1, 101) and intercommissural diameters (FIG. 1, 102). To ensure repeatability of measurements, the AP diameter of the mitral annulus is measured along the line that bisects the aortic root at the level of the mitral annulus. This line also crosses the geometrical center of the annulus. The CC diameter is measured in the direction perpendicular to the AP diameter and passing through the annular geometrical center. Note that while the CC diameter is often parallel with the coaptation line of the leaflets, it does not represent the leaflet apposition length.

Figure 10:
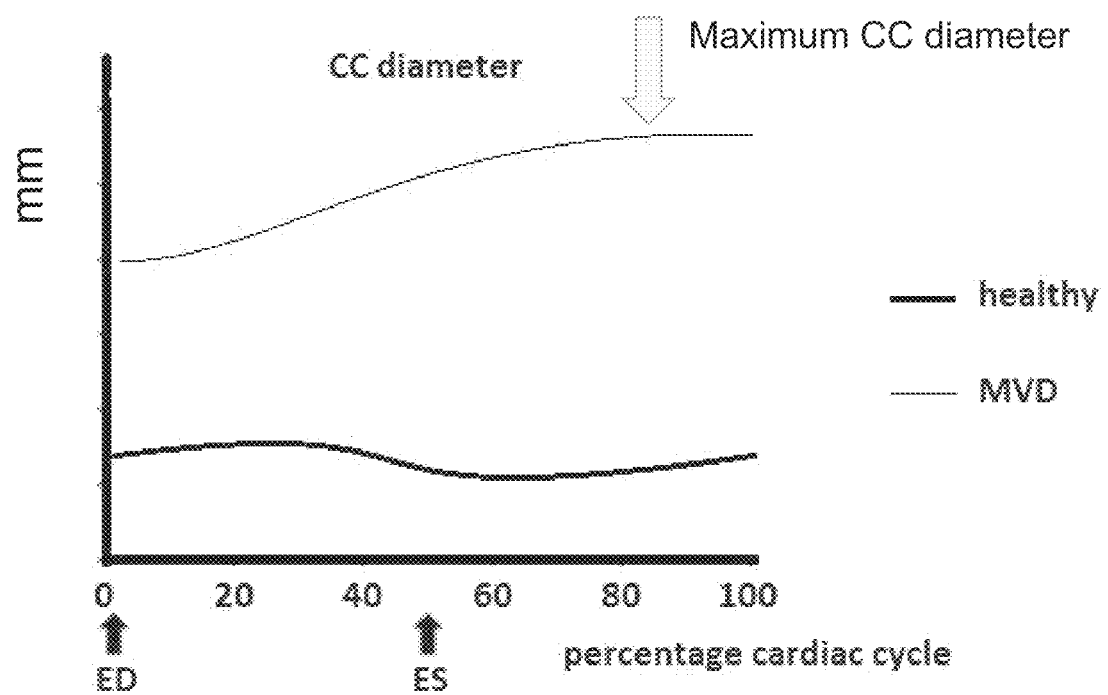
FIG. 10 shows the determined dynamically changing CC diameter and the corresponding maximum CC diameter in the case of an MVD patient.

In healthy patients, the CC diameter does not change significantly during the cardiac cycle. In DMVD patients the CC diameter increases from diastolic throughout systolic phase, while in healthy patients the CC diameter is slightly smaller in systole than in diastole as can be seen in FIG. 10.

Dynamic analysis of the CC diameter can therefore provide information regarding illness of the patient. The maximum CC diameter is an important factor in for instance valve repair therapy as it can be a measure for the number of chords that are necessary for the procedure.

In order for the clinician to determine if a valve replacement therapy is desirable, the ratio between the AP diameter and the CC diameter is also determined. The ratio is a measure for circularity of the mitral annulus. The higher the ratio, the less circular the mitral annulus is increasing risks for the patient regarding paravalvular leakage or left ventricular outflow track (LVOT) obstruction. A very large ratio is a contraindication to TMVR. This ratio can be computed for each phase during the cardiac cycle providing additional information to the clinical in how the circularity behavior the valve is during the cardiac cycle.

Figure 11:
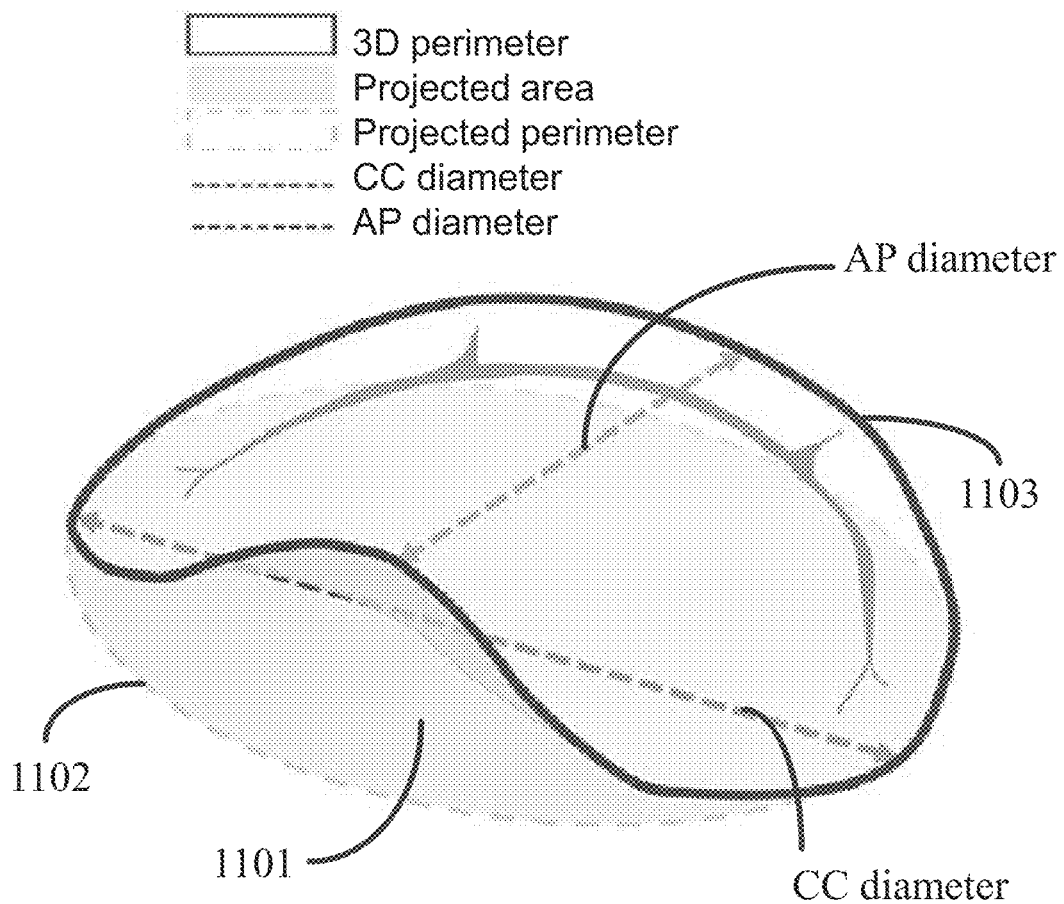
FIG. 11 shows the definition of the projected area and perimeter of the mitral annulus.

Another important parameter for dynamic analysis is the projected area (1101) and projected perimeter (1102) of the annulus as can be seen in FIG. 11 which present an example for the mitral valve. The projected area (1101) and projected perimeter (1102) is defined as the projection of the points of the 3D annulus contour (1103) onto its best fit plane. The projected area and perimeter are then calculated.

A robust way to calculate the annulus center and plane is as follows: First the annulus curve is discretized in small (for example 1 mm) steps, producing a set of 3D points. Then the annulus normal is calculated from this set of 3D points, for instance using principal component analysis. The center is simply the average of all discretized steps. Together the center and normal define a plane, this is the annulus plane.

The projected points are found by calculating the point on the annulus plane closest to each of the discretized points. From that, the projected perimeter can be calculated by adding the distances between the projected points. The projected area can for instance be calculated by methods well known in the art such as the Surveyor's Area Formula, as described in Bart Braden, "The Surveyor's Area Formula". The College Mathematics Journal 1986. 17 (4): 326-337.

As described before, the maximum projected area can be used to determine the expected amount of cinching that is needed to obtain coaptation of the valve leaflets. The maximum projected perimeter can be used by the clinician to determine the length of the annuloplasty ring that is necessary to perform the valve repair therapy.

Other parameters that can be of importance for the dynamic analysis of the mitral annulus are annulus height (FIG. 1, 103), 3D perimeter (FIG. 11, 1103), intertrigonal distance and the like.

Figure 12:
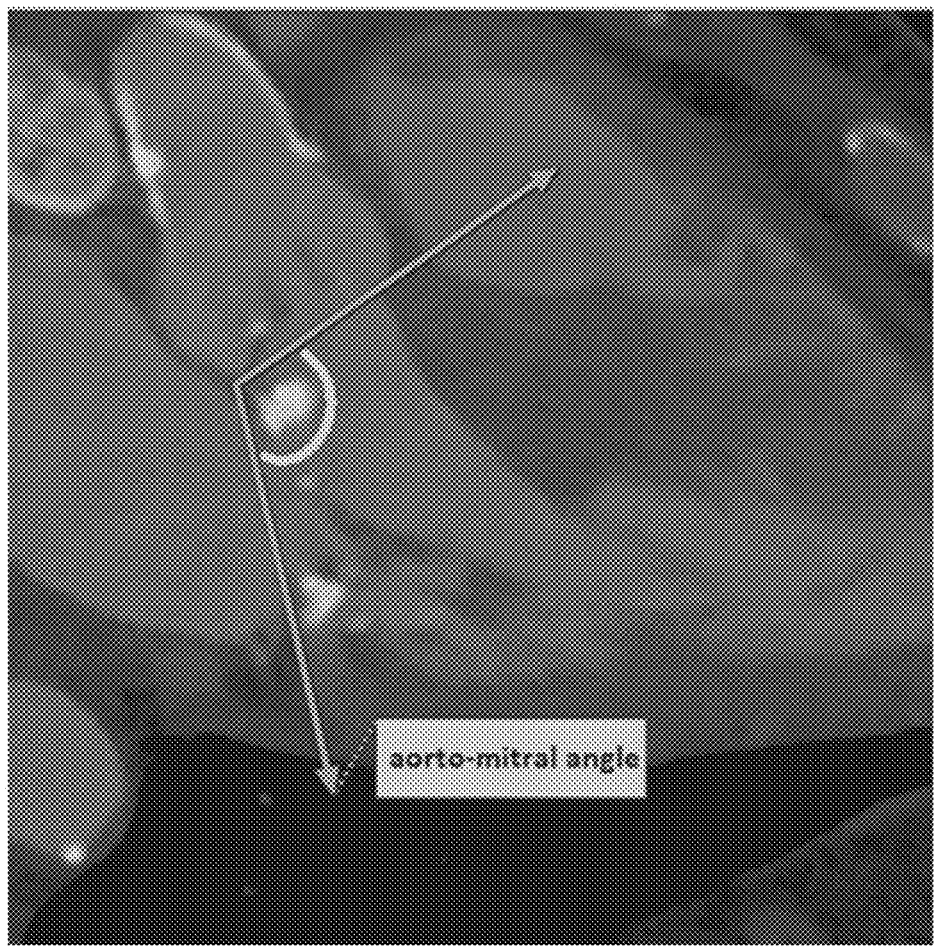
FIG. 12 shows the definition of the aorto-mitral angle.
Figure 13:
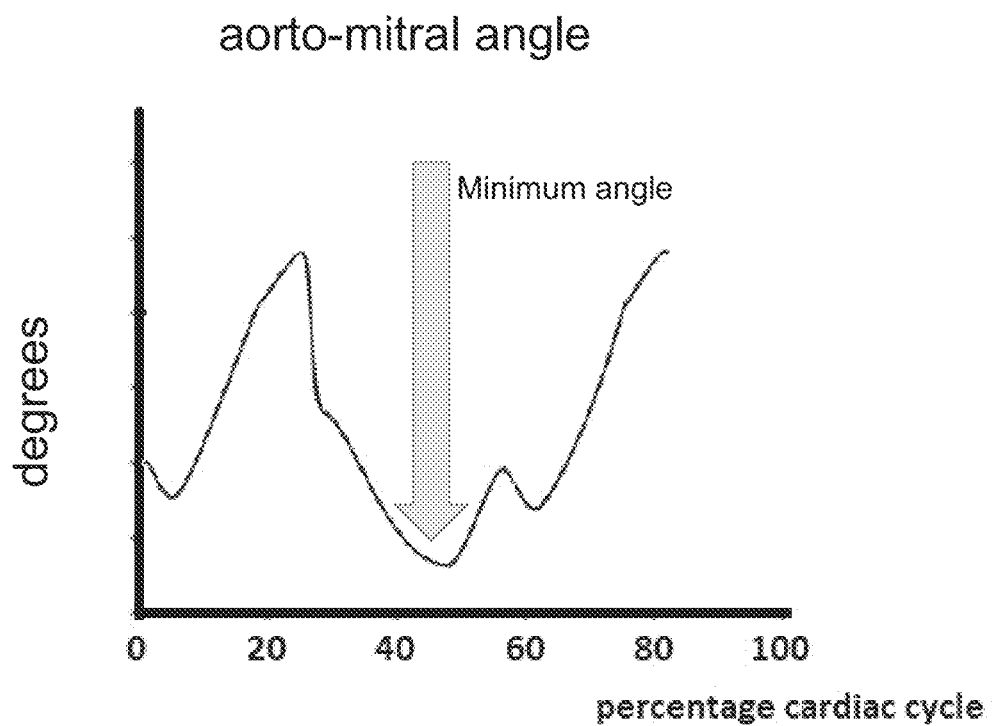
FIG. 13 shows the dynamic changes of the aorto-mitral angle during the cardiac phase.
Figure 14:
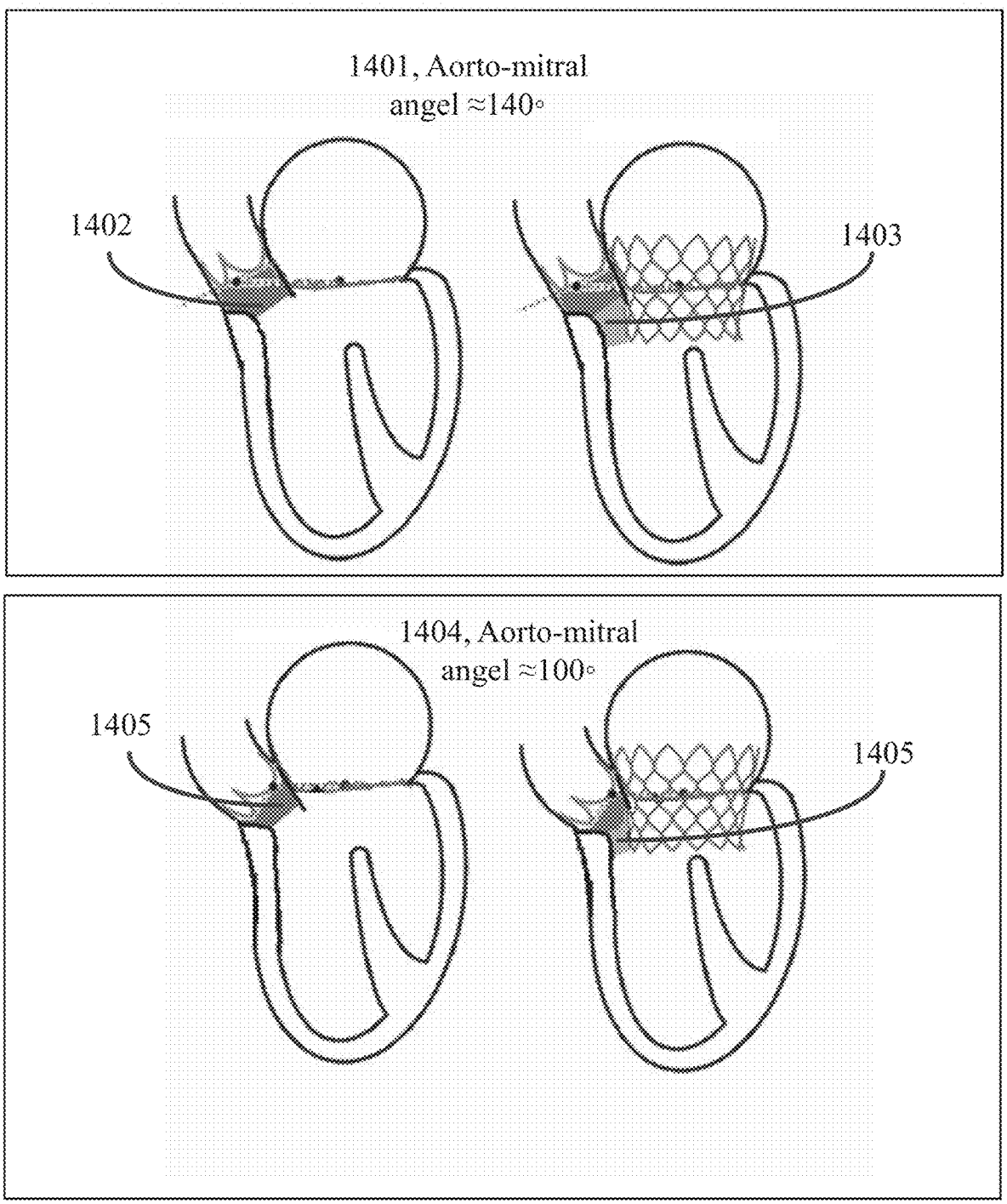
FIG. 14 shows the correlation between the aorto-mitral angle and the risk for LVOT obstruction.

Besides the annular anatomy and geometry, LVOT dimensions with respect to the annulus plane are of great importance for the expected landing zone of a replacement device. An important parameter regarding LVOT dimensions is for instance the aorto-mitral angle. The aorto-mitral angle is defined as the angle between the aortic annulus plane and the mitral annulus plane as can be seen in FIG. 12. The aorta annulus plane is defined as the plane derived from the three aortic nadir points. The aorto-mitral angle varies significantly during the cardiac cycle as can be seen in FIG. 13. The minimal aorto-mitral angle during the cardiac cycle can be used by the clinician to determine the risk of LVOT obstruction when performing a valve replacement procedure. The smaller the aorto-mitral angle, the more overlap there is between the LVOT and the valve implant landing zone as can be seen in FIG. 14, resulting in a smaller Neo-LVOT area. A large overlap can cause an obstruction of the LVOT due to the valve implant. This may be a contraindication for TMVR. FIG. 14 represent two different angles for the aorto-mitral angle, (1401) provides a schematic illustration in case the aorto-mitral angle is large and (1404) provides a schematic illustration in case the aorto-mitral angle is small. The LVOT is presented by (1402) in case of large aorto-mitral angle and (1405) in case of small aorto-mitral angle. The difference in Neo-LVOT area (1403) and (1405) between small and large aorto-mitral angle is shown in FIG. 14.

Other parameters that can be of importance for the dynamic analysis are the distance of the papillary to the mitral valve centroid, the projected distance of the papillary to the mitral plane, the left trigone, to the right trigone distance, the distance from the mitral annulus to the septal endocardium, inter-papillary distances and the like.

Figure 15:
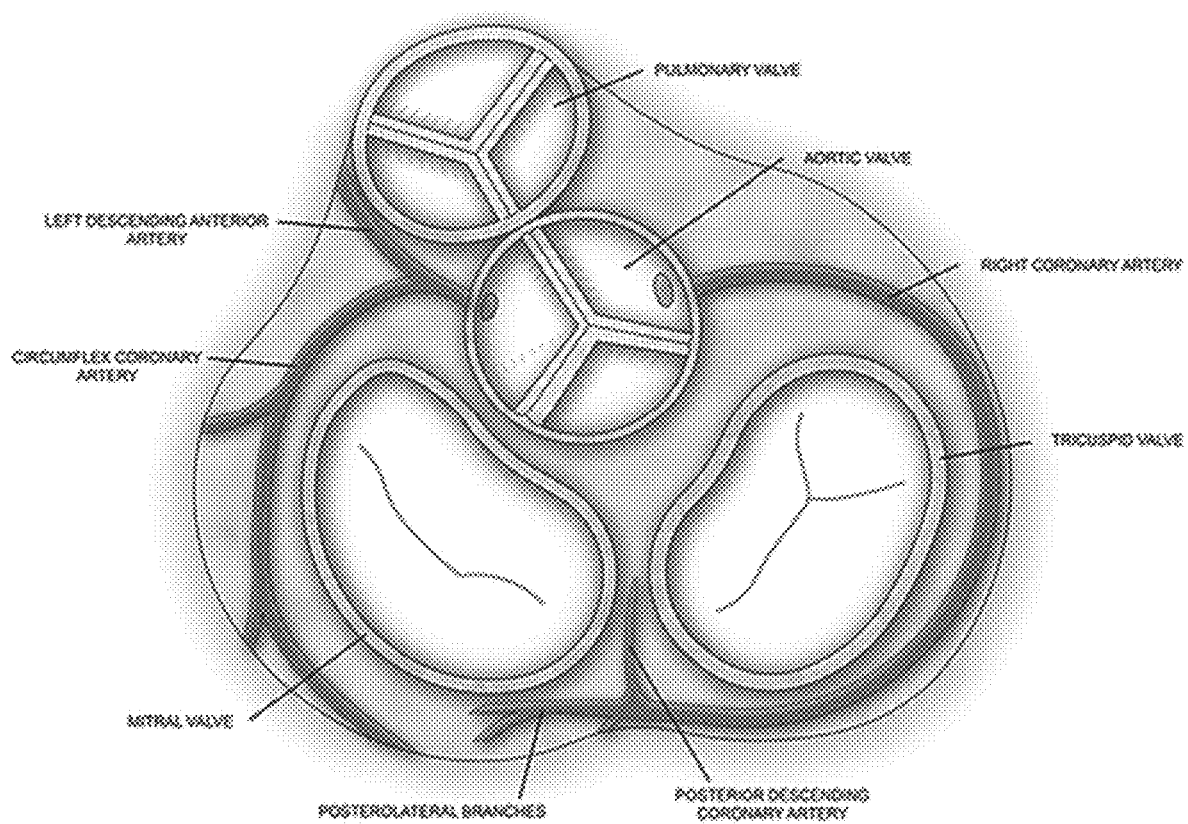
FIG. 15 shows the anatomy of the right coronary artery in relation to the tricuspid annulus.

When the valve replacement and repair therapies are for the tricuspid valve, additional parameters can be of importance. For instance the course of the right coronary artery (RCA) to tricuspid valve annulus. As can be seen in FIG. 15, the right coronary artery runs in close proximity of the tricuspid annulus. For the analysis the clinician indicates the centerline of the RCA. This can be done for instance by indicating two or more points within the right coronary artery within the 4D CT dataset. The Euclidean distance between each centerline point and the nearest point of the tricuspid annulus is then determined and this for each phase in which the tricuspid annulus has been segmented or just in one phase. Direct injury to the right coronary artery as a result of reparative operation on the tricuspid valve is a factual risk. Injury can for instance be caused by the anchoring mechanism of the ring used for the tricuspid valve repair. The minimal distance within the cardiac cycle between the RCA and the tricuspid valve annulus at a certain position of the annulus is therefore an important parameter for the clinician. If the minimum distance is too small, this could be a contraindication of tricuspid valve repair.

Figure 16:
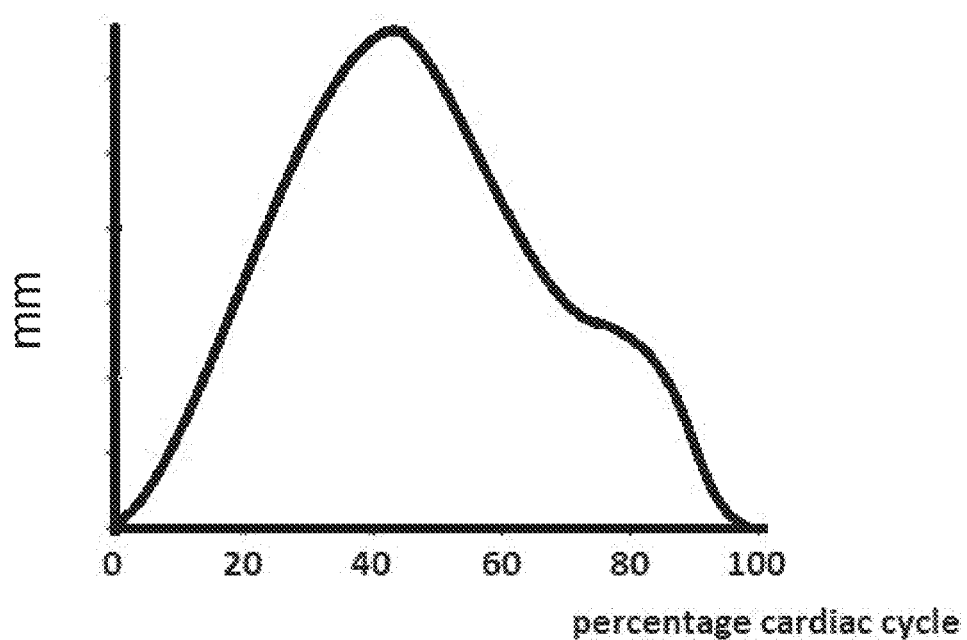
FIG. 16 shows the dynamic displacement of the tricuspid annulus during the cardiac cycle.

Another important parameter is the displacement of the tricuspid valve annulus, as for instance the tricuspid annular plane systolic excursion (TAPSE) measurement. This displacement (TAPSE) changes dynamically during the cardiac cycle as can be seen in FIG. 16 and is a measure for right ventricle function. In healthy patients the tricuspid annulus moves toward the apex during systole and returns to its resting position in diastole. In patients with large displacement of the tricuspid valve annulus, it is for instance preferable to use a non-rigid ring when performing annuloplasty.

Other parameters that can be of importance for the dynamic analysis of the tricuspid anatomy and geometry are the distance from right coronary artery to the anterior tricuspid leaflet insertion, the distance from right coronary artery to the posterior tricuspid leaflet insertion, the distance from the tricuspid valve annulus to the right ventricular apex and the like.

Figure 17:
FIG. 17 shows an example of a graphical user interface with the presentation of the AP diameter to the clinician.

The accurate and reproducible results of the dynamic analysis are shown to the clinician in a clear manner as for instance as shown in FIG. 17. Within FIG. 17, graph 1701 shows the AP diameter as it varies over the cardiac cycle. Within view 1701, different parameter can be selected by menu 1706, for instance CC diameter, projected area, projected perimeter and the like. View 1702 is a multi-planar reconstruction (MPR) short axis view (cross-sectional view), showing the AP diameter measurement (1703) within a specific phase. Views 1704 is a long axis MPR that can be used to locate view 1702. View 1705 is a volume render view, with transparent blood, clipped at the MPR plane in view 1704.

The present disclosure mainly describes the objects of interest as the heart valves. The skilled person would appreciate that this teaching can be equally extended to objects. For instance, the left atrium appendix of the heart. Furthermore, the present disclosure refers to CT datasets (in several forms). The skilled person would appreciate that this teaching can be equally extended to other imaging modalities, for instance rotational angiography, MRI, SPECT, PET, Ultrasound, X-ray, or the like.

Figure 18:
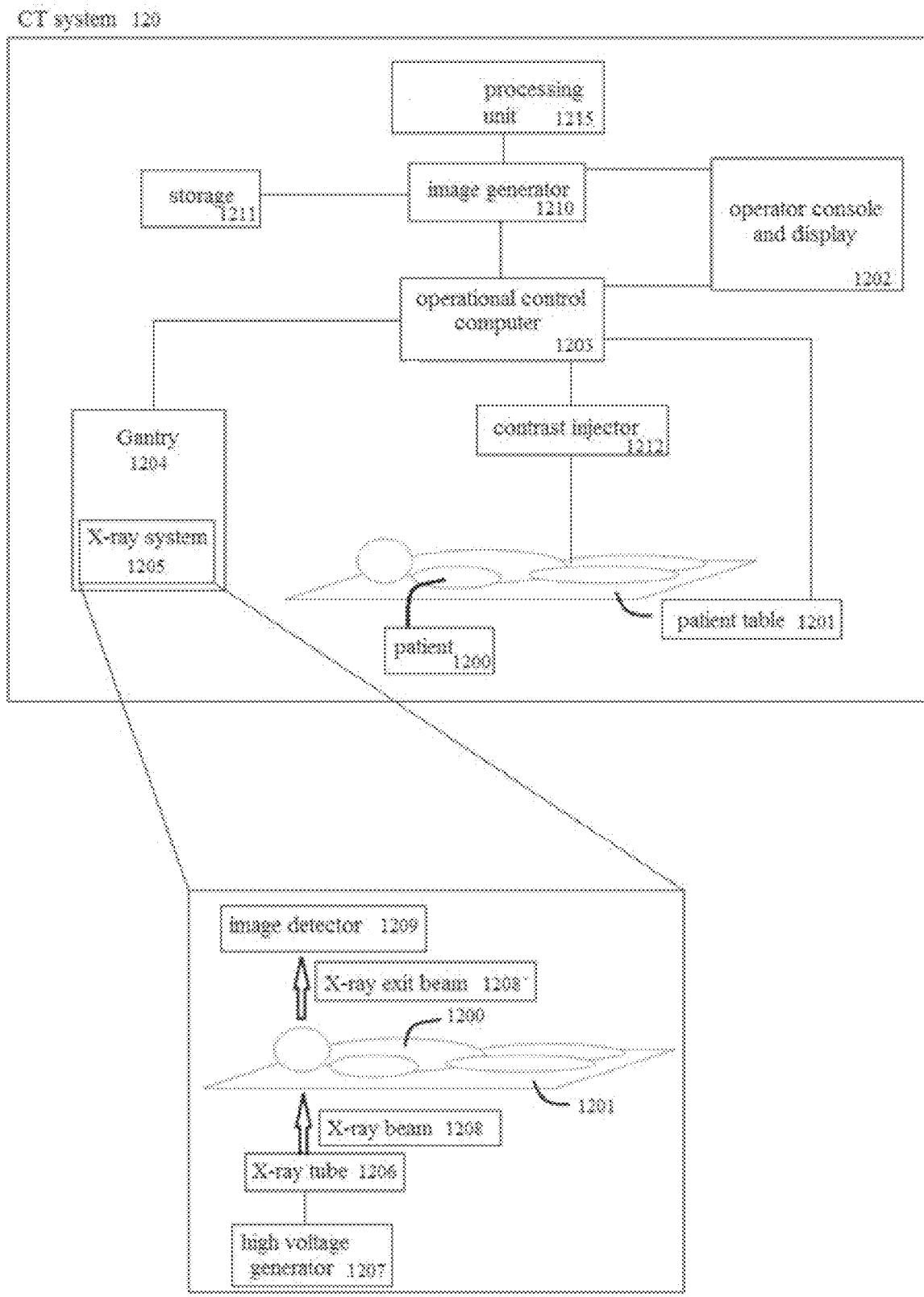
FIG. 18 shows a high-level block diagram of an example of an X-ray CT system.

The embodiment of this disclosure can be used on a standalone system or included directly in, for instance, a computed tomography (CT) system. FIG. 18 illustrates an example of a high-level block diagram of a computed tomography (CT) system. In this block diagram the embodiment is included as an example how the present embodiment could integrate in such a system.

Portions of the system (as defined by various functional blocks) may be implemented with dedicated hardware, analog and/or digital circuitry, and/or one or more processors operating program instructions stored in memory.

The most common form of computed tomography is X-ray CT, but many other types of CT exist, such as positron emission tomography (PET) and single-photon emission computed tomography (SPECT).

The CT system of FIG. 18 describes an X-ray CT system. In an X-ray CT system an X-ray system moves around a patient in a gantry and obtains images. Through use of digital processing a three-dimensional image is constructed from a large series of two-dimensional angiographic images taken around a single axis of rotation.

For a typical X-ray CT system 120 an operator positions a patient 1200 on the patient table 1201 and provides input for the scan using an operating console 1202. The operating console 1202 typically consists of a computer, a keyboard/foot paddle/touchscreen and one or multiple monitors.

An operational control computer 1203 uses the operator console input to instruct the gantry 1204 to rotate but also sends instructions to the patient table 1201 and the X-ray system 1205 to perform a scan.

Using a selected scanning protocol selected in the operator console 1202, the operational control computer 1203 sends a series of commands to the gantry 1204, the patient table 1201 and the X-ray system 1205. The gantry 1204 then reaches and maintains a constant rotational speed during the entire scan. The patient table 1201 reaches the desired starting location and maintains a constant speed during the entire scan process.

The X-ray system 1205 includes an X-ray tube 1206 with a high voltage generator 1207 that generates an X-ray beam 1208.

The high voltage generator 1207 controls and delivers power to the X-ray tube 1206. The high voltage generator 1207 applies a high voltage across the vacuum gap between the cathode and the rotating anode of the X-ray tube 1206.

Due to the voltage applied to the X-ray tube 1206, electron transfer occurs from the cathode to the anode of the X-ray tube 1206 resulting in X-ray photon generating effect also called Bremsstrahlung. The generated photons form an X-ray beam 1208 directed to the image detector 1209.

An X-ray beam 1208 consists of photons with a spectrum of energies that range up to a maximum determined by among others the voltage and current submitted to the X-ray tube 1206.

The X-ray beam 1208 then passes through the patient 1200 that lies on a moving table 1201. The X-ray photons of the X-ray beam 1208 penetrate the tissue of the patient to a varying degree. Different structures in the patient 1200 absorb different fractions of the radiation, modulating the beam intensity.

The modulated X-ray beam 1208' that exits from the patient 1200 is detected by the image detector 1209 that is located opposite of the X-ray tube.

This image detector 1209 can either be an indirect or a direct detection system.

In case of an indirect detection system, the image detector 1209 consists of a vacuum tube (the X-ray image intensifier) that converts the X-ray exit beam 1208' into an amplified visible light image. This amplified visible light image is then transmitted to a visible light image receptor such as a digital video camera for image display and recording. This results in a digital image signal.

In case of a direct detection system, the image detector 1209 consists of a flat panel detector. The flat panel detector directly converts the X-ray exit beam 1208' into a digital image signal.

The digital image signal resulting from the image detector 1209 is passed to the image generator 1210 for processing. Typically, the image generation system contains high-speed computers and digital signal processing chips. The acquired data are preprocessed and enhanced before they are sent to the display device 1202 for operator viewing and to the data storage device 1211 for archiving.

In the gantry the X-ray system is positioned in such a manner that the patient 1200 and the moving table 1201 lie between the X-ray tube 1206 and the image detector 1209.

In contrast enhanced CT scans, the injection of contrast agent must be synchronized with the scan. The contrast injector 1212 is controlled by the operational control computer 1203.

An embodiment of the present application is implemented by the X-ray CT system 120 of FIG. 18 as follows. A clinician or other user acquires a CT scan of a patient 1200 by selecting a scanning protocol using the operator console 1202. The patient 1200 lies on the adjustable table 1201 that moves at a continuous speed during the entire scan controlled by the operational control computer 1203. The gantry 1204 maintains a constant rotational speed during the entire scan Multiple two-dimensional X-ray images are then generated using the high voltage generator 1207, the X-ray tube 1206, the image detector 1209 and the digital image generator 1210 as described above. This image is then stored on the hard drive 1211. Using these X-ray images, a three-dimensional image is constructed by the image generator 1210.

The processing unit 1215 uses the three-dimensional image to perform the dynamic analysis as described above. The processing unit 1215 can be a microprocessor, microcontroller, digital signal processor, or general purpose computer. Alternatively or additionally, the processing unit 1215 may include discrete electronic components (integrated circuitry), such as one or more Application Specific Integrated Circuits (ASICs) and/or programmable logic devices (e.g., a Field Programmable Gate Arrays (FPGAs)).

Some of the methods and processes described above, can be implemented as computer program logic for use with the processing unit 1215. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

There have been described and illustrated herein several embodiments of a method and apparatus for dynamically analyzing valve parameters, based on the information extracted from multiple heart phases.

While particular embodiments of the present application have been described, it is not intended that the present application be limited thereto, as it is intended that the present application be as broad in scope as the art will allow and that the specification be read likewise.

For example, the data processing operations can be performed offline on images stored in digital storage, such as a picture archiving and communication system (PACS) commonly used in the medical imaging arts. It will therefore be appreciated by those skilled in the art that yet other modifications could be made to the provided application without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art.

Similarly, any necessary files for performing the functions attributed to the computers, servers or other network devices may be stored locally and/or remotely, as appropriate.

Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above.

The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser.

It should be appreciated that alternate embodiments may have numerous variations from that described above. For example, customized hardware might also be used and/or particular elements might be implemented in hardware, software (including portable software, such as applets) or both.

Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the present application as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the present application to the specific form or forms disclosed, but on the contrary, the intention is to cover all modifications, alternative constructions and equivalents falling within the spirit and scope of the present application, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open ended terms (i.e., meaning "including, but not limited to,") unless otherwise noted. The term "connected," when unmodified and referring to physical connections, is to be construed as partly or wholly contained within, attached to or joined together, even if there is something intervening.

Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members.

Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the present application. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein.

Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein. Including:

P. Theriault-Lauzier et al, "Quantitative multi-slice computed tomography assessment of the mitral valvular complex for transcatheter mitral valve interventions part 1: systematic measurement methodology and inter-observer variability", EuroIntervention. 2016 Oct. 10; 12(8): e1011-e1020.

P. Theriault-Lauzier et al, "Quantitative multi-slice computed tomography assessment of the mitral valvular complex for transcatheter mitral valve interventions part 2: geometrical measurements in patients with functional mitral regurgitation", EuroIntervention. 2016 Oct. 10; 12(8): e1021-e1030.

The invention claimed is:

1. A method for dynamically assessing a heart valve from a sequence of consecutive volumetric image frames of such heart valve, which images are separated in time by a certain time interval and refer to different phases of a heart cycle, the method comprising:
   a) identifying the heart valve in at least one image of the sequence;
   b) segmenting the heart valve to identify a contour of the heart valve, wherein the contour of the heart valve corresponds to an annulus of the heart valve
   c) propagating the contour of the heart valve as identified in b) to other images of the sequence; and
   d) performing dynamic analysis of the heart valve based on the contour of the heart valve as propagated in c);
   wherein the identification of the contour of the heart valve in b) involves
      i) determining a center-lumen line within a ventricle of the heart that is connected to the heart valve by adjusting the center-lumen line towards a center of mass of a ventricle blood pool,
      ii) determining an apex point within the ventricle from the center-lumen line of i), and
      iii) determining a long axis of the heart from the apex point of ii).

2. A method according to claim 1, wherein the identification of the contour of the heart valve in b) further involves:
   receiving from a user a seed point indicating a center of the heart valve;
   using the seed point and the apex point of ii) to determine the long axis of the heart in iii);

determining a cost image representing probability that a voxel belongs to the contour of the heart valve from the long axis of the heart as determined in iii);

finding a minimal cost path within the cost image, wherein the minimal cost path corresponds to the contour of the heart valve; and transforming points of the minimal cost path to 3D coordinates to obtain a 3D representation of the contour of the heart valve.

3. A method according to claim 1, wherein:
the long axis of the heart is determined in iii) using a seed point to estimate location of the apex point of the ventricle and the center-lumen line within the ventricle.

4. A method according to claim 2, wherein:
the cost image has the form of a matrix wherein columns represent a distance along the long axis of the heart in which the center column corresponds to the position of the seed point on the long axis of the heart and rows represent the degree of rotation around the long axis of the heart, wherein the value of each element of the cost image corresponds to distance from the long axis of the heart to an edge of a blood lumen for a combination of distance along the long axis of the heart and an angle.

5. A method according to claim 1, further comprising:
adjusting points on the contour of the heart valve using annulus seeding points, and
calculating for each annulus seeding point a cross-sectional plane containing a center of the heart valve.

6. A method according to claim 5, wherein:
the cross-sectional plane is allowed to move along a normal vector of such cross-sectional plane.

7. A method according to claim 5, wherein:
any adjustment of the points on the contour of the heart valve within either a cross-section view or a cross-sectional plan view or a volume rendered view is automatically transferred to all views.

8. A method according to claim 1, wherein:
propagating the contour of the heart valve in c) comprises registering all or part of the images of the sequence to find a transformation and applying such transformation to contour points of the segmented heart valve to find corresponding locations in other images of the sequence.

9. A method according to claim 8, wherein:
the registration is performed on a sub volume within the sequence of images, such sub volume being user defined or automatically extracted based on the location of the heart valve as segmented.

10. A method according to claim 8, wherein:
the transformation is a non-rigid transformation configured to model changing shape of the heart.

11. A method according to claim 1, wherein:
the consecutive images frames of the sequence are part of a 4D CT dataset.

12. A method according to claim 1, wherein:
the dynamic analysis of d) comprises calculating at least one parameter related to geometry and/or geometry deformation of the heart valve in a plurality of images of the sequence.

13. A method according to claim 12, wherein:
the at least one parameter is selected from the group consisting of: anteroposterior (AP) diameter, intercommissural (CC) diameter, height of the annulus, perimeter of the annulus, projected area of the annulus, projected perimeter of the annulus, and combinations thereof.

14. A non-transitory computer product directly loadable into memory of a digital computer and comprising software code portions for performing the method according to claim 1 when the computer product is run on a computer.

15. An apparatus for acquiring a series of three-dimension images, the apparatus comprising:
means for obtaining a cine of consecutive image voxels of the heart of a patient; and
a processor configured to perform the method according to claim 1 to perform a dynamic analysis of a valve of the heart.

16. An apparatus according to claim 15, wherein:
the cine of consecutive image voxels comprises a CT dataset.

17. A method for dynamically assessing a heart valve from a sequence of consecutive volumetric image frames of such heart valve, which images are separated in time by a certain time interval and refer to different phases of a heart cycle, the method comprising:
identifying the heart valve in at least one image of the sequence;
receiving from a user a seed point indicating a center of the heart valve;
using the seed point to determine a long axis of the heart by estimating a location of an apex point within a ventricle of the heart that is connected to the heart valve and a center-lumen line within the ventricle, wherein the center-lumen line is determined by adjusting the center-lumen line towards a center of mass of a ventricle blood pool;
determining a cost image representing probability that a voxel belongs to a contour of the heart valve from the long axis of the heart, wherein the contour of the heart valve corresponds to an annulus of the heart valve;
finding a minimal cost path within the cost image, wherein the minimal cost path corresponds to the contour of the heart valve;
transforming points of the minimal cost path to 3D coordinates to obtain a 3D representation of the contour of the heart valve;
propagating the contour of the heart valve as obtained to other images of the sequence; and
performing dynamic analysis of the heart valve based on the contour of the heart valve as propagated.

18. A method according to claim 17, wherein:
the apex point within the ventricle is determined from the center-lumen line.

19. A method according to claim 17, wherein:
the heart valve comprises a mitral heart valve or a tricuspid heart valve, and the ventricle comprises a left ventricle or a right ventricle.

20. A method according to claim 1, wherein:
the heart valve comprises a mitral heart valve or a tricuspid heart valve, and the ventricle comprises a left ventricle or a right ventricle.

21. A method according to claim 12, wherein:
the heart valve comprises a mitral heart valve; and
the at least one parameter is selected from the group consisting of: LVOT (Left Ventricular Outflow Track) dimensions with respect to an annulus plane; aorto-mitral angle; distance between the papillary and mitral heart valve centroid; projected distance between the papillary to mitral valve plane; distance between the left trigone and the right trigone; distance between the mitral annulus and the septal endocardium; inter-papillary distance; and combinations thereof.

22. A method according to claim 12, wherein:

the heart valve comprises a tricuspid heart valve; and the at least one parameter is selected from the group consisting of: minimal distance during a heart cycle between a right coronary artery and the tricuspid heart valve annulus at a certain position of the tricuspid heart valve annulus, displacement of the tricuspid heart valve annulus; distance between a right coronary artery and the anterior tricuspid leaflet insertion; distance between a right coronary artery and the posterior tricuspid leaflet insertion; distance between the tricuspid heart valve annulus and the right ventricular apex; and combinations thereof.

\* \* \* \* \*